(12) United States Patent
Halpern et al.

(10) Patent No.: US 11,442,071 B2
(45) Date of Patent: Sep. 13, 2022

(54) REUSABLE ELECTROCHEMICAL SENSORS CAPABLE OF CYCLODEXTRIN INTERACTIONS AND METHODS OF USE THEREOF

(71) Applicant: UNIVERSITY OF NEW HAMPSHIRE, Durham, NH (US)

(72) Inventors: Jeffrey M. Halpern, Durham, NH (US); McKenna Merrill, Durham, NH (US)

(73) Assignee: University of New Hampshire, Durham, NH (US)

( * ) Notice: Subject to any disclaimer, the term of this patent is extended or adjusted under 35 U.S.C. 154(b) by 510 days.

(21) Appl. No.: 16/453,121

(22) Filed: Jun. 26, 2019

(65) Prior Publication Data

US 2019/0391166 A1 Dec. 26, 2019

Related U.S. Application Data

(60) Provisional application No. 62/689,956, filed on Jun. 26, 2018.

(51) Int. Cl.
*G01N 33/74* (2006.01)
*G01N 27/327* (2006.01)

(52) U.S. Cl.
CPC ....... *G01N 33/743* (2013.01); *G01N 27/3275* (2013.01)

(58) Field of Classification Search
None
See application file for complete search history.

(56) References Cited

PUBLICATIONS

K. Patel, et al., "Enzyme-Responsive Snap-Top Covered Silica Nanocontainers", Journal of the American Chemical Society, 130(8): p. 2382-2383, Feb. 2008.*
Boland et al., "Designing Stable Redox-Active Surfaces: Chemical Attachment of an Osmium Complex to Glassy Carbon Electrodes Prefunctionalized by Electrochemical Reduction of an In Situ-Generated Aryldiazoniumu-Generated Aryldiazonium Cation." Langmuir 2008, 24, 6351-6358.
Cappadona et al., "Host-Guest Complex of β-Cyclodextrin and Disulfide Form of 4-Aminothiophenol." Appl. Sci. 2012, 2, 773-779; doi:10.3390/app2040773.
Loftsson et al., "Cyclodextrins in drug delivery." Expert Opin. Drug. Deliv. (2005) 2(2): 335-351.
Loftsson et al., "Self-association of cyclodextrins and cyclodextrin complexes." J. Pharm. Sci., vol. 93, Issue 5: 1091-1099, May 2004.
Pio Di Cagno, Massimiliano, "The Potential of Cyclodextrins as Novel Active Pharmaceutical Ingredients: A Short Overview." Molecules 2017, 22, 1; doi:10.3390/molecules22010001.
Sambasevam, et al., "Synthesis and Characterization of the Inclusion Complex of β-cyclodextrin and Azomethine." Int. J. Mol. Sci. 2013, 14, 3671-3682; doi:10.3390/ijms14023671.
Tao et al., "Temperature-Sensitive Electrochemical Recognition of Tryptophan Enantiomers Based on B-Cyclodextrin Self-Assembled on Poly (L-GlutamicAcid)." Anal. Chem. 2014, 86, 2633-2639.

* cited by examiner

*Primary Examiner* — J. Christopher Ball
(74) *Attorney, Agent, or Firm* — Pierce Atwood LLP

(57) ABSTRACT

Electrochemical sensor surfaces capable of detecting cortisol at low and high concentrations using cyclodextrin interactions are described. One electrochemical sensor surface uses a cyclodextrin:adamantane complexed surface. Another electrochemical sensor surface uses one or more rotaxanes of surface-bound cyclodextrin.

19 Claims, 25 Drawing Sheets

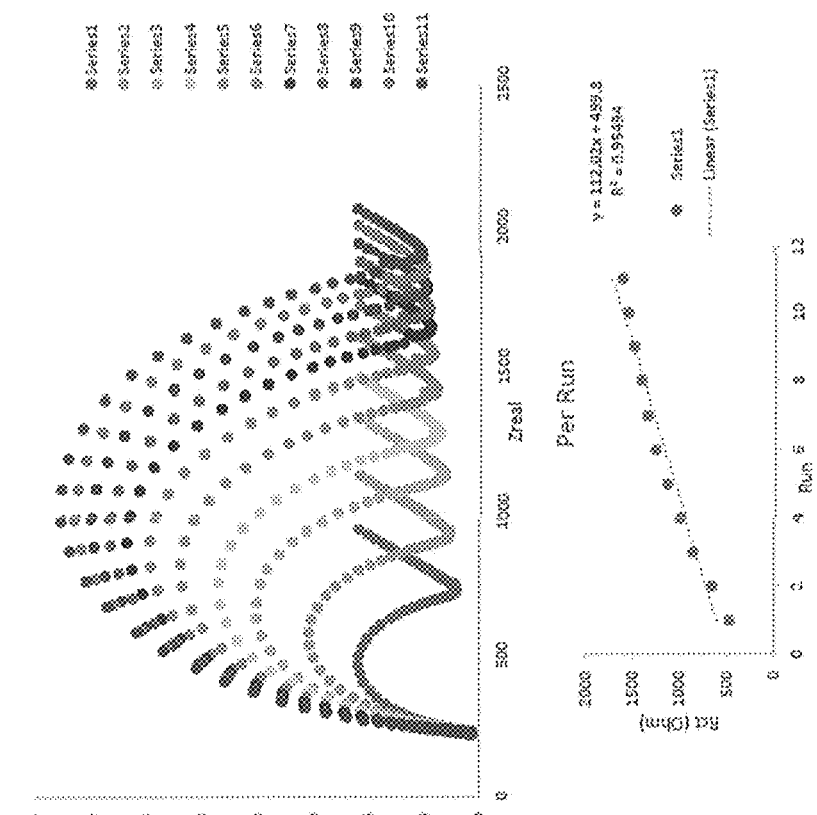
FIG. 3C
FIG. 3A
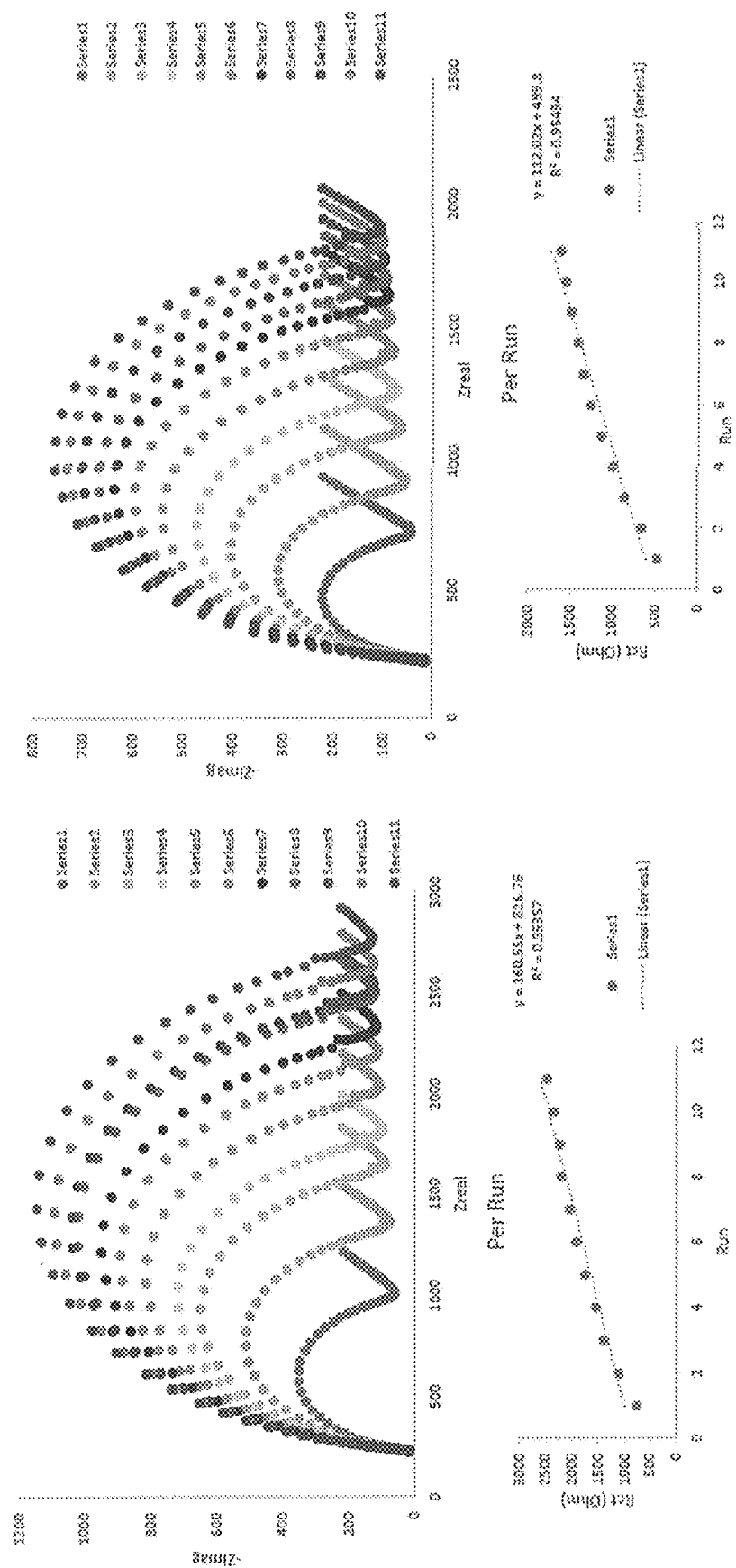
FIG. 3D
FIG. 3B

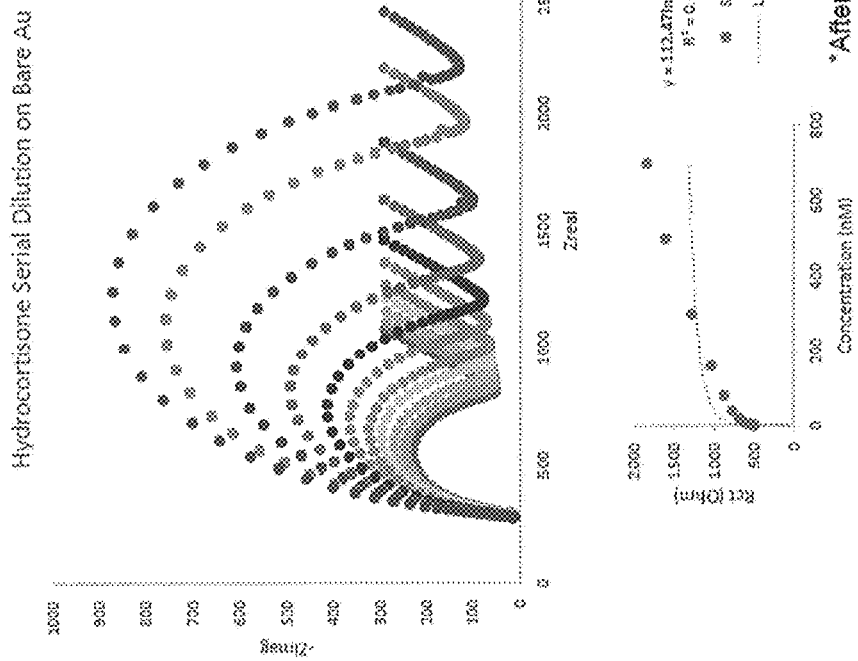
FIG. 5C
FIG. 5D
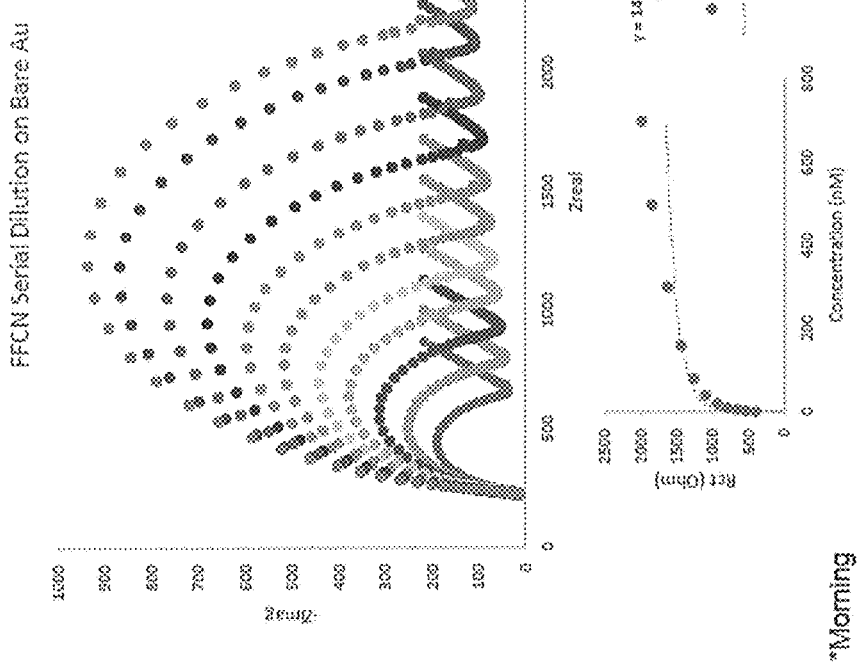
FIG. 5A
FIG. 5B

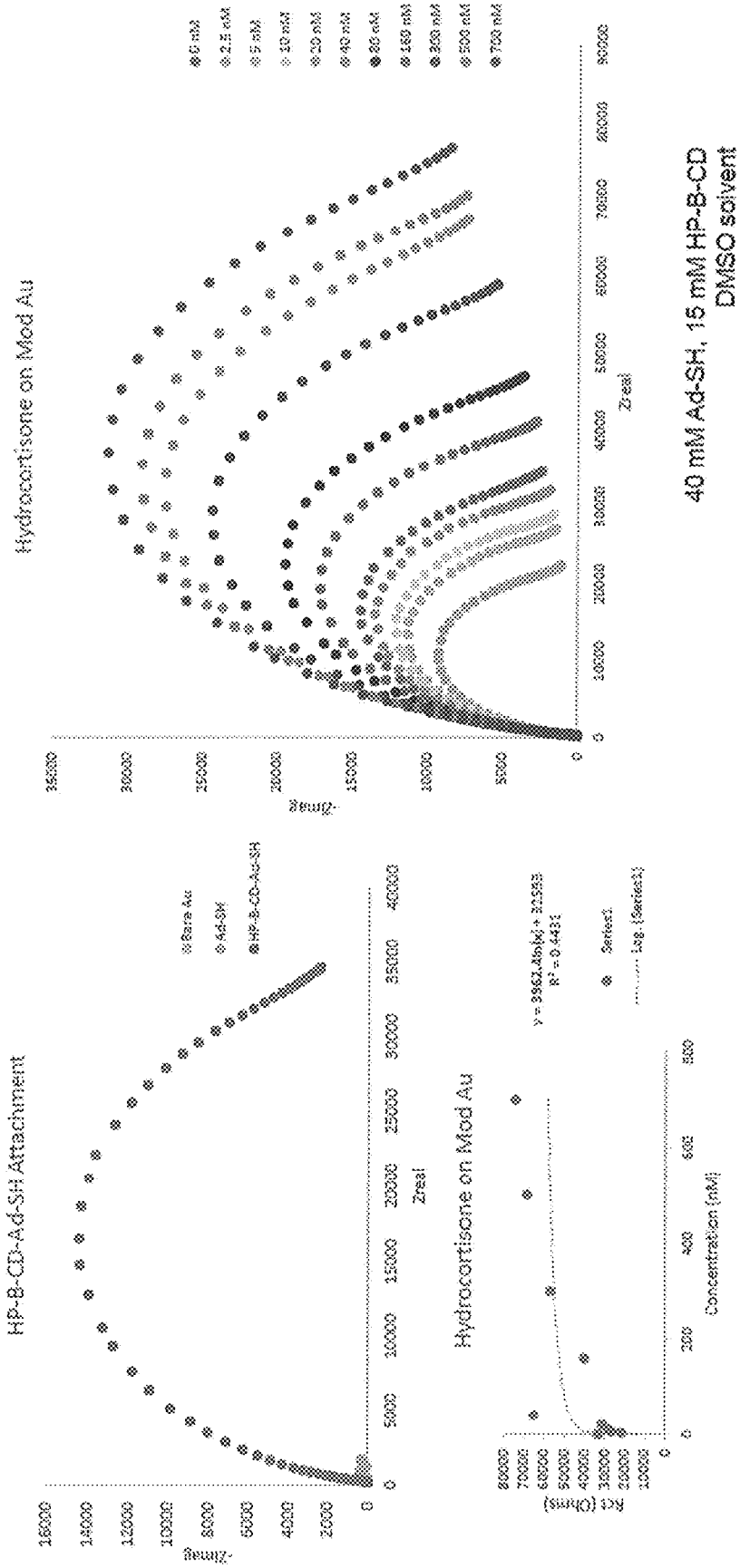
FIG. 7C
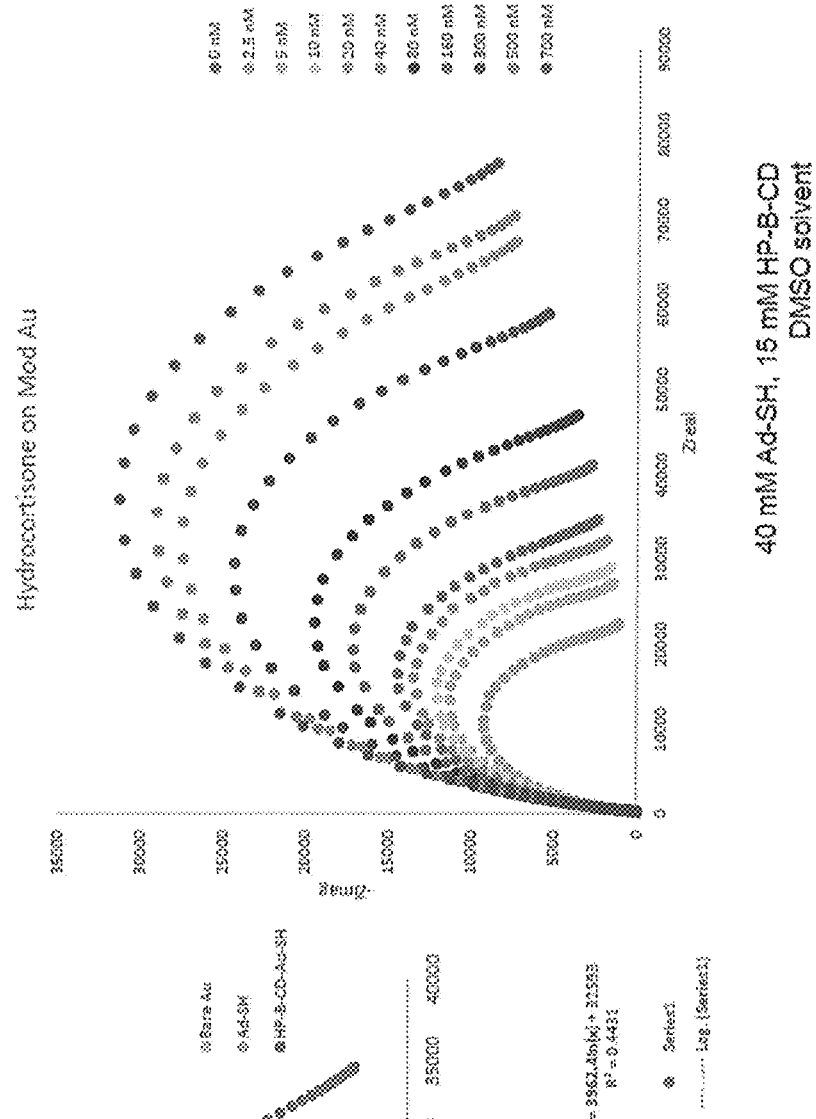
FIG. 7A
FIG. 7B

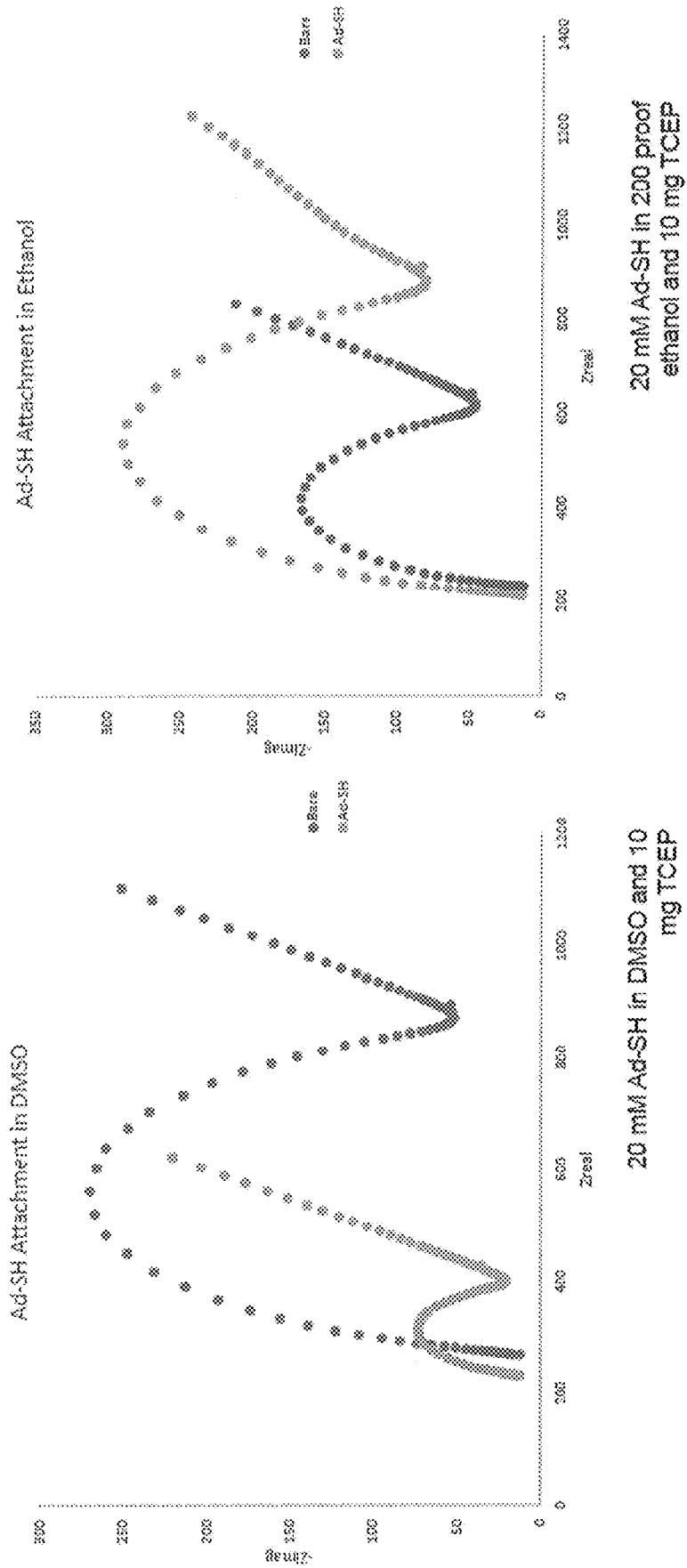

| Frequency/ cm-1 | Functional group and type of vibration |
|---|---|
| 1750 | Aromatic C=C bond<br>Ketone C=O stretch |
| 1360 | $NO_2$ stretch or $CH_3$ bend |
| 1260 | C-H (methyl)<br>C=S stretch |
| 1150 | C-O alcohol (tertiary) |
| 1080 | C-O stretch (Ether) |
| 946 | C-H bending<br>Trans RCH=CHR |

REUSABLE ELECTROCHEMICAL SENSORS CAPABLE OF CYCLODEXTRIN INTERACTIONS AND METHODS OF USE THEREOF

CROSS-REFERENCE TO RELATED APPLICATION

This application claims benefit under 35 U.S.C. § 119(e) of U.S. Provisional Patent Application No. 62/689,956, filed Jun. 26, 2018, the contents of which is incorporated hereby by reference in its entirety.

BACKGROUND OF THE INVENTION

In times of adversity, human bodies respond differently to stress. This stress response is often coupled with a change in blood pressure or release of steroid hormones, such as adrenaline and cortisol. Cortisol is a stress biomarker that is correlated to various diseases, including Addison's disease, Cushing's syndrome, Post-Traumatic Stress Disorder (PTSD), and Human Immunodeficiency Virus (HIV). For example, Cushing's Syndrome is associated with high cortisol levels. For further example, Addison's Disease is associated with low cortisol levels. Cortisol levels can be an indicator of the overall health and balance of the adrenal glands and regulation of blood pressure. Consequently, quantifying cortisol levels from serum is advantageous in treatment therapies.

Present means of detecting cortisol, along with other hormones, include urinary or blood analysis via immunoassays, which quantify the amount of unbound hormones present in blood. The enzyme-linked immunosorbent assay (ELISA) is a popular technique due to its accuracy and reliability. While ELISA is highly accurate, it is difficult to operate in a standard, public clinic due to its cost and intricate sample processing. An alternative cortisol immunosensor was constructed by Florida Institute of Technology using cortisol-specific antibodies that bind specifically with cortisol. However, antibodies have limited shelf-life and batch-to-batch variation.

SUMMARY OF THE INVENTION

The present disclosure provides embodiments of various electrochemical sensors that are capable of detecting cortisol and other hydrophobic analytes at low and high concentrations using cyclodextrin interactions. Electrochemical sensors of the present disclosure are reusable, cheaper, and faster than current sensing techniques.

According to an aspect of the invention, electrochemical sensors are provided, the sensors including a surface modified with a covalently attached monolayer configured to non-covalently attach to cyclodextrin and release cyclodextrin based on contact with a binding analyte. In certain embodiments, the electrochemical sensor includes an electrode. In some embodiments, the electrode comprises a metal. In some embodiments, the electrode includes at least one of gold, carbon, platinum, silicon, silicon dioxide, and silver. In certain embodiments, the monolayer includes adamantane. In some embodiments, the adamantane is attached to cyclodextrin. In embodiments, the monolayer includes a carboxylic acid. In certain embodiments, the monolayer includes a rotaxane. In some embodiments, the rotaxane includes at least one of polyethylene glycol (PEG), polypropylene glycol (PPG), and polyisobutylene glycol (PBG).

According to another aspect of the invention, methods of generating an electrochemical sensor capable of performing a cyclodextrin interaction are provided, the methods including modifying a surface of the electrochemical sensor of any embodiment of an aforementioned aspect of the invention with adamantane; and non-covalently attaching cyclodextrin to the adamantane.

According to another aspect of the invention, methods of generating an electrochemical sensor capable of performing a cyclodextrin interaction are provided, the methods including modifying a surface of the electrochemical sensor of any embodiment of an aforementioned aspect of the invention with at least one carboxylic acid; and non-covalently attaching cyclodextrin to the at least one carboxylic acid.

According to another aspect of the invention, methods of generating an electrochemical sensor capable of performing cyclodextrin interaction are provided, the methods including modifying a surface of the electrochemical sensor of any embodiment of an aforementioned aspect of the invention with a rotaxane that includes cyclodextrin.

According to another aspect of the invention, methods for hydrophobic molecular recognition for electrochemical sensing are provided, the methods including contacting a sample with an electrochemical sensor that includes a surface modified with a covalently attached monolayer configured to non-covalently attach to cyclodextrin and release cyclodextrin based on contact with a binding analyte; and monitoring release of cyclodextrin from the surface. In certain embodiments, a means of monitoring the release of cyclodextrin comprises at least one of electrochemical impedance spectroscopy, amperometric monitoring, voltametric monitoring, and potentiometric monitoring. In some embodiments, the method also includes reloading the surface with cyclodextrin. In some embodiments, reloading the surface is performed after monitoring the release of cyclodextrin from the surface. In some embodiments, re-charging the surface includes rinsing the surface with an organic solvent, the organic solvent comprising at least one of dimethyl sulfoxide (DMSO), methanol, ethanol, chloroform, dimethylformamide (DMF), and tetrahydrofuran (THF); and contacting the rinsed surface with a cyclodextrin solution. In certain embodiments, the cyclodextrin solution is an about 15 mM cyclodextrin solution. In some embodiments, the cyclodextrin solution is in a range of between 1 µM to at least 50 mM cyclodextrin. In some embodiments, the method also includes monitoring the release of cyclodextrin from the surface. In certain embodiments, the method also includes monitoring the release of cyclodextrin for about 1 millisecond to about 45 minutes. In some embodiments, the method also includes monitoring the release of cyclodextrin for about 30 minutes to about 45 minutes. In some embodiments, the method also includes monitoring the release of cyclodextrin for about 5 minutes to about 10 minutes. In certain embodiments, the method also includes modifying the surface with adamantane using a thiol self-assembled monolayer with a tris(2-carboxyethyl)phosphine (TCEP) reducing agent. In some embodiments, modifying the surface includes creating an adamantane-thiol mixture of about 20 mM to about 40 mM of adamantane-thiol in about 0.35 mM TCEP and dimethyl sulfoxide (DMSO)/ethanol. In some embodiments, modifying the surface includes contacting the surface with the adamantane-thiol mixture. In certain embodiments, the method also includes contacting the surface with the adamantane-thiol mixture for about 16 hours to about 24 hours. In some embodiments, the method also includes rinsing the contacted surface with an organic solvent including at least one of dimethyl sulfoxide (DMSO), methanol, ethanol, chloroform, dimethylformamide (DMF), and tetrahydrofuran (THF). In certain embodiments, the method also includes confirming attachment of adamantane to the rinsed surface by performing at least one of quartz crystal microbalance (eQCM) and electrochemical impedance spectroscopy (EIS). In some embodiments, the method also includes contacting the rinsed surface with a cyclodextrin solution to create the electrochemical sensor that includes the surface modified with covalently attached monolayer configured to non-covalently attach to cyclodextrin and release cyclodextrin based on contact with a binding analyte. In certain embodiments, the cyclodextrin solution is about 15 mM. In some embodiments, the method also includes preparing the cyclodextrin solution in phosphate-buffered saline (PBS). In certain embodiments, the method also includes contacting the sonicated surface with the cyclodextrin solution for up to about 1.5 hours.

BRIEF DESCRIPTION OF THE DRAWINGS

For a more complete understanding of the present disclosure, reference is now made to the following description taken in conjunction with the accompanying drawings.

FIG. 2A(1) shows an embodiment in which a surface is be modified with about 500 MW PEG via thiol gold interaction. FIG. 2A(2) shows the modified surface contacted with an α-cyclodextrin solution to form one or more surface bound rotaxanes. The transition shown from FIG. 2A(1) to FIG. 2A(2) illustrates the loading of the electrochemical sensor's surface with cyclodextrin. The transition shown from FIG. 2A(2) to FIG. 2A(1) illustrates the unloading of cyclodextrin from the electrochemical sensor's surface. The transition shown from FIG. 2A(2) to FIG. 2A(3) illustrates that the surface can be calibrated to double layer capacitance change when exposed to analytes. FIG. 2B illustrates reloading during steps illustrated in FIG. 2A(1) and FIG. 2A(2). FIG. 2C illustrates results of detection of about 2.5 nM to about 40 nM cortisol.

FIG. 3A-D provides results of control experiments conducted prior to modifying a sensor surface according to certain embodiments of the present disclosure. FIGS. 3A and 3C illustrate Nyquist plots of successive runs of EIS without altering setup at different times of day. FIGS. 3B and 3D correspond to the Nyquist plots, FIG. 3A and FIG. 3B, respectively and compare the Rct behavior with the run at which it was observed. Abbreviations used in FIG. 3A-D and elsewhere herein are as follows: Rct=charge transfer resistance, Zimag=imaginary or out of phase version of the impedance, and Zreal=real or in phase version of the impedance.

FIG. 4A shows results of a serial dilution with bare Au. FIG. 4C represents a control serial dilution mimicking a serial dilution containing an analyte of interest. The analyte was left out in order to determine if the addition of volume contributed to nonspecific Rct patterns. The slope provided in the graph shown in FIG. 4B, which represents the linear pattern of Rct increase of "Bare Au" (FIG. 4A), and the slope provided in the graph shown in FIG. 4D, which represents the linear pattern of Rct increase of "FFCN Serial Dilution on Bare Au," (FIG. 4C). The results demonstrate that the slope of the graph of "Bare Au" (FIG. 4B) is nearly identical to that of "FFCN Serial Dilution on Bare Au," (FIG. 4D) indicating no additional Rct changes are caused by volume addition.

FIG. 5A-D illustrates a $Fe(CN)_6^{3-/4-}$ serial dilution as a control compared to a hydrocortisone serial dilution according to certain embodiments of the present disclosure. FIG. 5A is identical to the "FFCN Serial Dilution on Bare Au" plot shown in FIG. 4C. The graph shown in FIG. 5B was altered from the graph shown in FIG. 4D in order to compare Rct patterns with mimicked analyte concentrations in order to compare slopes with the serial dilution, which is represented in FIGS. 5C and 5D. Concentrations are provided in the Nyquist plot shown in FIG. 5C. The Nyquist plot shown in FIG. 5C represents a hydrocortisone serial dilution on a bare Au electrode.

FIG. 7A-C illustrates a Nyquist plot monitoring an adamantane-hydroxypropyl-β-cyclodextrin attachment, a hydrocortisone serial dilution using this modification, and a graph for the serial dilution relating Rct to analyte concentration according to certain embodiments of the present disclosure. Results shown were obtained from a second attempt at the attachment and serial dilution, showing similar behaviors as represented in FIG. 6A-C. FIG. 7A shows a Nyquist plot monitoring an adamantane-hydroxypropyl-β-cyclodextrin attachment, FIG. 7B shows a graph for the serial dilution relating Rct to analyte concentration, and FIG. 7C shows a hydrocortisone serial dilution using this modification, according to embodiments of the invention.

FIG. 8A illustrates an expected Rct increase coupling the thiol attachment. Rct significantly decreases to a value less than that achieved when the electrode was bare. FIG. 8B shows a graph for the serial dilution relating Rct to analyte concentration and FIG. 8C shows results of a hydrocortisone serial dilution using this modification according to embodiments of the invention.

FIG. 9A-B illustrates a comparison of thiol attachments in different solvents with identical preparation and treatment procedures according to certain embodiments of the present disclosure. The plot in FIG. 9A shows a response when dimethyl sulfoxide was used and the plot in FIG. 9B shows a response when 200-proof ethanol was used.

FIG. 19A-F graphs correspond to points 1-6, respectively, as displayed in FIG. 18.

FIG. 20A shows results from the first use of the sensor, FIG. 20B shows results from the second use of the sensor, and FIG. 20C shows results from the third use of the sensor.

FIG. 21B provides a graph of concentration versus relative capacitive change for the sensor in FIG. 21A.

FIG. 22A shows that cortisol does not respond. FIG. 22B shows that the bare electrode has minimal response. FIG. 22C shows that with cortisol without cyclodextrin there is no response. FIG. 22D shows that β-cyclodextrin doesn't interact with a PEG surface.

FIG. 24A provides traces of an FTIR signal confirming cyclodextrin being removed and added to the surface. FIG. 24B provides data showing the frequency/cm$^{-1}$ for various functional groups and types of vibration.

DETAILED DESCRIPTION

Figure 1:
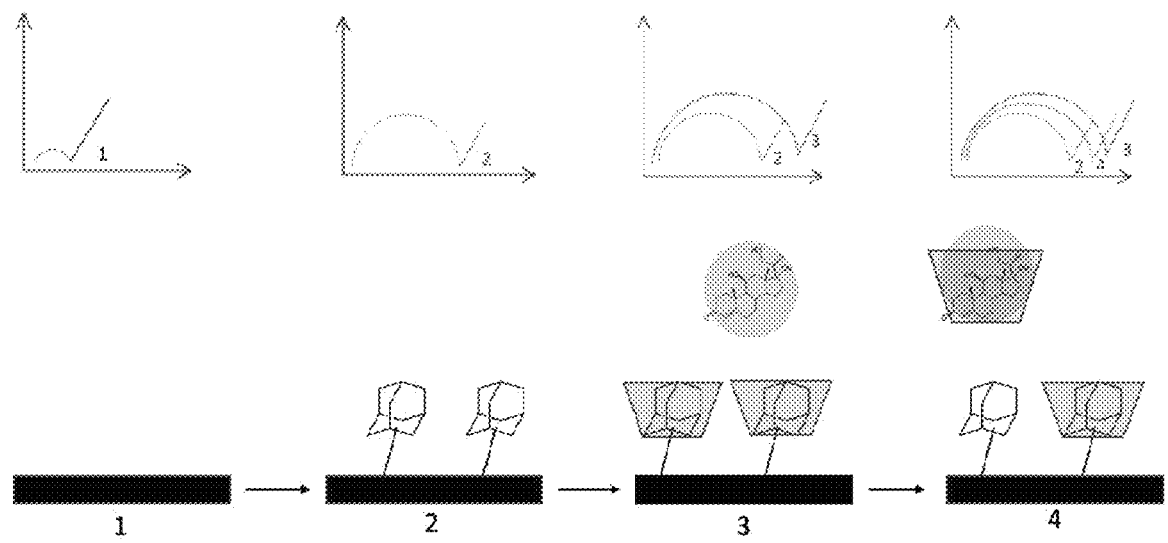
FIG. 1 illustrates an embodiment of the creation and use of an electrochemical sensor with a cyclodextrin:adamantane complexed surface according to embodiments of the present disclosure.

Certain aspects of the present disclosure relate to cyclodextrin-based reproducible sensors in which surface modification is renewable. Hydrophobic molecules, like common steroid hormones and phospholipids, have a valuable characteristic in that their polarities allow them to be targeted using supramolecular chemistry. Cyclodextrin, forms of which include α-cyclodextrin, β-cyclodextrin, and γ-cyclodextrin, is a cyclic supramolecule that exhibits a hydrophobic, nonpolar cavity and a hydrophilic, polar exterior. This allows cyclodextrin to form non-covalent, host-guest inclusion complexes with hydrophobic molecules in aqueous solutions. The host-guest molecule ratios of cyclodextrin with "guest" molecules may be a 1:1 host-guest complex ratio, a 2:1 host:guest ratio, or a 1:2 host:guest ratio. Certain embodiments of the invention may include host-guest complexes having more complicated complexation ratios of cyclodextrin and guest molecule(s). It is envisioned that, in certain embodiments of the invention, 1, 2, 3, or more different complex ratios may be included. Although not wishing to be bound to a particular theory, the primary driving force for creating a host-guest inclusion complex may be defined by the competitive polarities of its guest molecules. Because cyclodextrin's cavity is nonpolar, it tends to favor molecules that are similarly nonpolar, a non-limiting example of which is cortisol. Cortisol and β-cyclodextrin share a large association constant, $K_a$, of 17200-3000 $M^{-1}$ in aqueous solution, indicative of a highly favorable inclusion formation.

In certain embodiments of the invention, a cyclodextrin is one or more of an α-cyclodextrin, a β-cyclodextrin, and a γ-cyclodextrin. A non-limiting example of a cyclodextrin-based reproducible sensor of the invention is a cortisol sensor. In some aspects of the invention, one or more molecules, such as, but not limited to adamantane and one or more rotaxane forming polymers may be attached to a surface of a sensor of the invention. In certain embodiments, cyclodextrin is attached to an adamantane and/or surface polymers to form rotaxane(s). The adamantane and/or rotaxane(s) form a stable host-guest complex with the cyclodextrin. Thus, when a suitable hydrophobic analyte is introduced and contacts the sensor, cyclodextrin may release from the surface because of a more favorable complex formation with the analyte than to the surface with adamantane and/or surface polymers to form rotaxane(s). In some embodiments of the invention, a suitable hydrophobic analyte comprises cortisol. This competitive nature between the surface and the analyte is a beneficial sensing paradigm in that it creates renewable sensor modification, enhances the otherwise semi-specific properties of cyclodextrin, and generates a sensor that can be tailored to recognize a class of hydrophobic molecules depending on their ability to disrupt the surface complex.

Previously, cyclodextrin has been used in nanoparticle hybrid systems, fluorescence sensing, and drug delivery systems for its inclusion complex formation. Sensors of the present disclosure are beneficial over these prior uses because cyclodextrin, as used with and included in the herein disclosed sensors, acts as a mobile sensing mechanism rather than a permanent modification, and the level of sensor mobility depends and can be determined based on its relationship with the analytes with which it is present. Sensors of the present disclosure are also advantageous in their potential sensing application towards hydrophobic molecules such as, but not limited to, cortisol and hydrophobic steroid hormones other than cortisol, glycophospholipids, steroids, testosterone, estradiol, phospholipids, etc. Additional molecules for which sensors of the invention may be utilized for sensing and determination are known in the art, see for example: Loftsson, T. et al., Expert Opin Drug Del. 2, 335-351 (2005); Loftsson, T. et al. J. Pharm. Sci. Vol 93, No. 5:1091-1099 (2004); Cappadona, T. A. et al., *Appl. Sci.* 2012, 2, 773-779; Sambasevam, K. P. et al., *Int. J. Mol. Sci.* 2013, 14, 3671-3682; Pio di Cagno, M.

Molecules 2017, 22, 1; doi:10.3390/molecules22010001, the content of each of which is incorporated by reference herein in its entirety.

Because of cyclodextrin's general affinity for hydrophobic molecules, cyclodextrin is capable of binding to other molecules, simultaneously. For example, though not intended to be limiting, an embodiment of a sensor of the invention may be contacted with an sample or analyte comprising 1, 2, 3, or more different hydrophobic molecules with affinity to cyclodextrin, therefore, methods and sensors of some embodiments of the invention may be tailored such that they may be used to distinguish between nonspecific environmental changes and changes in a molecule of interest. Electrochemical Impedance Spectroscopy (EIS) may be used as a detection technique in certain aspects of the invention. EIS is ultra-sensitive to the environment and provides the ability to analyze the sensors' interaction with its environment and other hydrophobic molecules in the presence of a molecule of interest.

While the present disclosure describes the use of cyclodextrin, other macromolecules may be used in certain embodiments of the invention. As used herein, a "macromolecule" refers to a large molecule that may be created by polymerization of smaller subunits. In at least some embodiments, a macromolecule may include thousands of atoms.

Adamantane-Bound Cyclodextrin Mediated Electrochemical Sensor Surface

Certain embodiments of an electrochemical sensor of the present disclosure are capable of monitoring cyclodextrin binding of hydrophobic analytes by using a cyclodextrin: adamantane complexed surface. While the present disclosure describes the use of adamantane and surface bound polymers that form rotaxane(s), certain embodiments of the invention encompass sensors and methods in which other chemical compounds that interact with cyclodextrin may be used, such as mercaptopropionic acid, or other molecules, terminated on the surface, that form inclusion complexes. Additional molecules that interact with cyclodextrin are suitable for use in methods and sensors of the invention are known in the art and can be utilized by the skilled artisan.

An adamantane-modified surface of an electrochemical sensor may be exposed to β-cyclodextrin to form a β-cyclodextrin:adamantane surface complex. The β-cyclodextrin may have various functional groups. A non-limiting list of cyclodextrin derivatives that may be used include hydroxy-propyl-β-cyclodextrin, carboxymethyl-β-cyclodextrin, hepatakis 6-sulfo-β-cyclodextrin, hepatakis 6-deoxy-6-amino-β-cyclodextrin, and methyl-β-cyclodextrin.

The β-cyclodextrin may be removed from the β-cyclodextrin:adamantane surface complex in the presence of hydrophobic content. The β-cyclodextrin may also be removed from the β-cyclodextrin:adamantane surface complex by contacting (e.g., rinsing) the surface with dimethyl sulfoxide (DMSO), methanol, ethanol, chloroform, dimethylformamide (DMF), tetrahydrofuran (THF), or another organic solvent. The organic solvents disrupt the β-cyclodextrin:adamantane affinity (i.e., disrupt non-covalent bonding of the β-cyclodextrin:adamantane surface). After the electrochemical sensor is contacted with a sample, resulting in at least some of the β-cyclodextrin being removed from the β-cyclodextrin:adamantane surface complex, β-cyclodextrin can be reattached to the adamantane modified surface of the electrochemical sensor by exposing the surface to a concentrated β-cyclodextrin solution.

Adamantane may be attached to a gold (Au) electrode by a thiol self-assembled monolayer with a tris(2-carboxyethyl) phosphine (TCEP) reducing agent (as illustrated in section 2 of FIG. 1) using the following methodology. A mixture of about 20 mM to about 40 mM adamantane-thiol may be created in 0.35 mM TCEP and DMSO/ethanol. A polished Au electrode may be contacted with the adamantane-thiol mixture for about 16 hours to about 24 hours. After contacting, the Au electrode may be rinsed with DMSO, methanol, ethanol, chloroform, dimethylformamide (DMF), tetrahydrofuran (THF), or another organic solvent, and thereafter sonicated (this step may be omitted as sonication may damage attachment of the monolayer to the electrode), resulting in an adamantane-modified surface. While use of an Au electrode is described, other types of electrodes may be used in embodiments of the invention, including but not limited to carbon electrodes, platinum electrodes, silicon electrodes, silicon dioxide electrodes, silver electrodes, and the like. If a carbon electrode is used, thionyl chloride followed by a Grignard reaction may be used to attach adamantane to the carbon electrode. Art-known methods can be used to attach adamantine to an electrode or another material such as silver, etc., see for example: Boland, S. et al. Langmuir (2008), 24, 6351-6358, the content of which is incorporated by reference herein.

Attachment of adamantane to an electrode, a non-limiting example of which is an Au electrode, may be confirmed by an increase in weight using quartz crystal microbalance (eQCM), an increase of impedance using electrochemical impedance spectroscopy (EIS), and/or other surface analysis techniques. EIS applies a sinusoidal current potential to an electrochemical cell and measures the current response. This current is inversely proportional to the flow of electrons between the working electrode surface and a ferri-ferrocyanide redox solution, commonly known as impedance. The impedance increases as chemicals are deposited or present on the electrode surface. FIG. 1 illustrates an embodiment of increased impedance. In view of the foregoing, an increased impedance is illustrated by a comparison of the graphs of FIG. 1, sections 1 and 2, whereby the graph in FIG. 1, section 1 illustrates impedance of an Au electrode and the graph in FIG. 1, section 2 illustrates impedance of an Au electrode with an adamantane modified surface.

The adamantane-modified surface may be contacted with a β-cyclodextrin solution to facilitate interaction of β-cyclodextrin with the adamantane-modified surface (as illustrated in FIG. 1, section 3). In some embodiments of the invention, the β-cyclodextrin solution may be about 10 mM to about 15 mM and the β-cyclodextrin solution may be created in phosphate-buffered saline (PBS). In certain embodiments, the Au electrode with the adamantane-modified surface may be contacted with the β-cyclodextrin solution for up to about 10 minutes, about 20 minutes, about 30 minutes, about 45 minutes, about 1.5 hours, or more, resulting in a β-cyclodextrin:adamantane surface complex having a 1:1 relationship. In other words, one β-cyclodextrin may interact with one surface bound adamantane. Impedance may increase as β-cyclodextrin is interacted with the surface bound adamantane (as illustrated by the graph in FIG. 1, section 3).

As stated, β-cyclodextrin may be removed from the β-cyclodextrin:adamantane surface complex in the presence of hydrophobic content. For example, though not intended to be limiting, the addition of cortisol may result in the removal of some, but not all, of the β-cyclodextrin due to competitive binding rates (as illustrated in FIG. 1, section 4). As the β-cyclodextrin is removed from the surface bound adamantane, impedance may be reduced (as illustrated by the graph in FIG. 1, section 4). Removal of the β-cyclodextrin from the surface bound adamantane may be observed as an impedance decrease and/or a mass decrease using EIS and/or eQCM, respectively. Removal of the β-cyclodextrin from the surface bound adamantane may also be observed using an amperometric method, a voltametric method, a potentiometric method, and/or optically. Monitoring release of the β-cyclodextrin from the surface bound adamantane may be observed at a time point or across a time period from about 1 millisecond to about 45 minutes, for example, though not intended to be limiting, at 10 msec, 100 msec, 10 sec, 1 min, 10 min, 20 min, 30 min, 40 min, 45 min, between 1 msec and 1 min., between 1 msec and 20 min, between 1 min and 45 min, etc. In some embodiments the time period begins at the time of contact with a competitive binding agent, a non-limiting example of which is cortisol. One skilled in the art may use routine methods to set monitoring times and to monitor release of cyclodextrin in embodiments of sensors of the invention.

A decrease in concentration may be tested by performing a reverse serial dilution from high concentration to lower concentration. Success of such reverse serial dilution testing likely depends on reloading of β-cyclodextrin on the surface bound adamantane.

In some aspects of the invention, the surface-bound adamantane is reloaded with cyclodextrin. To reload the surface bound adamantane (so the same electrochemical sensor may be used to test a subsequent sample), the electrode's surface may be contacted with DMSO, methanol, ethanol, chloroform, dimethylformamide (DMF), tetrahydrofuran (THF), or another organic solvent; then rinsed with methanol, DMSO, ethanol, chloroform, dimethylformamide (DMF), tetrahydrofuran (THF), or another organic solvent; then optionally sonicated (in some aspects of the invention, the sonication step is omitted because sonication may damage attachment of the monolayer to the electrode); and then re-contacted with a β-cyclodextrin solution. In some embodiments of the invention, the β-cyclodextrin solution may be about 10 mM to about 15 mM. Such β-cyclodextrin reloading and baseline rinse measurements demonstrate (1) electrode activity can be rejuvenated and can reestablish the original monolayer impedance level and (2) the removal of some fouling effects from biological media. In some embodiments of the invention, a reloading and rinsing procedure carried out following testing with EIS, comprises rinsing the electrode in ethanol and UHP, soaking the rinsed electrode in ethanol for 30 minutes, rinsing the electrode again in ethanol and UHP, and placing the electrode in β-cyclodextrin solution for 30-45 minutes, which is followed by a quick UHP rinse prior to EIS testing. Reloading of the sensors of the present disclosure is beneficial as compared to previously known sensors, which may require abrasive removal and reapplication of surface modifications in order for the sensor to be used again. The sensors of the present disclosure are able to be reused simply be reloading cyclodextrin due to the cyclodextrin being a secondary modification of the sensor surface.

An initially large, predictable, and repeatable surface impedance may be expected after each reloading of β-cyclodextrin. If the impedance does not return to predictable levels after reloading, surface characterization may need to be performed to determine inconsistencies. Using EIS and eQCM, an optimal contact time of the β-cyclodextrin solution with the adamantane-sensor surface may be determined.

The β-cyclodextrin-adamantane complexed surface of an electrochemical sensor may be exposed to different hydrophobic analytes with different β-cyclodextrin affinities. Non-limiting examples of such analytes include carotenoids (e.g., β-carotene and astaxanthin), cholesterol, estrogen, aldosterone, corticosterone, phenylalanine, decenolycarnitine, glycerophospholipids (e.g., lysoPC C14:0 and lysoPC C18:1), and the like. Changes in EIS signal may be used to identify competitive binding rates and capabilities of the β-cyclodextrin-adamantane complexed surface.

Competitive binding rates (i.e., analyte:β-cyclodextrin affinity) may be different if the surface terminal groups of β-cyclodextrin are changed. For example, adding a hydroxypropyl group to β-cyclodextrin changes the binding rates of β-cyclodextrin to cortisol, see for example, FIGS. 6 and 7 and corresponding description herein, which provide results from use of a β-cyclodextrin derivative in an embodiment of a sensor of the invention. Other β-cyclodextrin derivatives may be included in certain embodiments of the invention.

The electrochemical sensor may produce repeatable and reproducible signals, determined by multiple serial dilution calibration curves and control experiments. The electrochemical sensor may produce the same baseline and predictable analyte response without the need to polish or re-modify the surface of the electrochemical sensor. A different impedance response may be observed for each analyte and each supramolecule tested.

Rotaxane Electrochemical Sensor Surface

Another aspect of the invention includes embodiments comprising rotaxane electrochemical sensor surfaces. Fouling (e.g., the accumulation of unwanted material on the sensor surface) may arise in complex biofluid matrices. When fouling occurs, rinsing the electrochemical sensor with DMSO and ethanol may not be sufficient for deterring biofilm formation. Antimicrobial surfaces may be used to deter biofilm formation as well as a supramolecular mediated sensor surface.

Using a polymer-brush self-assembled monolayer, one or more rotaxanes of surface bound cyclodextrin may be achieved. A sensor with one or more rotaxanes of surface bound cyclodextrin may increase the range of the sensor and/or reduce fouling of the sensor surface in the detection of hydrophobic analytes. A rotaxane is an assembly with multiple supramolecules trapping a linear self-assembled polymer chain. For example, polyethylene glycol (PEG):α-cyclodextrin, polypropylene glycol (PPG):β-cyclodextrin, and polyiosbutylene (PBG):γ-cyclodextrin all form rotaxanes. Since multiple cyclodextrins can be added to the sensor surface, the range of the sensor may be increased using one or more rotaxanes.

PEG is a linear or branched hydrophilic inactive polyether compound available in a range of molecular weights. PEG has been reported as giving crystalline compounds in high yield with α-cyclodextrin.

The present disclosure is not limited to the user of PEG, PPG, or PBG in the formation of rotaxanes. For example, in certain embodiments of the invention, a PEG derivative, PPG derivative, and/or PBG derivative may be used. In at least some embodiments of the invention, a zwitterion of PEG, PPG, or PBG may be used. As used herein, a "zwitterion" refers to a molecule with two or more functional groups, of which at least one has a positive electrical charge and at least one has a negative electrical charge, such that the net charge of the entire molecule is zero. A derivative or zwitterion may be used because such may not change the functionality provided by an underlying PEG, PPG, or PBG molecule.

Figure 2A:
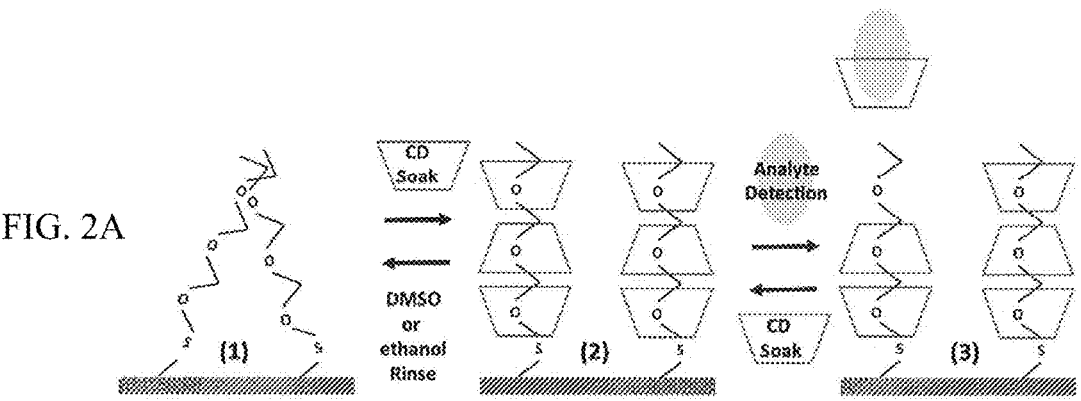
FIG. 2A-C illustrates the creation and use of rotaxane surfaces in an electrochemical sensor according to certain embodiments of the present disclosure.

In certain embodiments of the invention, a surface may be modified with about 500 MW PEG via thiol gold interaction [see FIG. 2A(1)]. The modified surface may be contacted with an α-cyclodextrin solution to form one or more surface bound rotaxanes [see FIG. 2A(2)]. In certain embodiments of the invention, a surface may be modified with about 500 MW PPG via thiol gold interaction, and the modified surface may be contacted with aβ-cyclodextrin solution to form one or more surface bound rotaxanes. In certain embodiments of the invention, a surface may be modified with about 500 MW PBG via thiol gold interaction, and the modified surface may be contacted with a γ-cyclodextrin solution to form one or more surface bound rotaxanes.

Figure 2B:
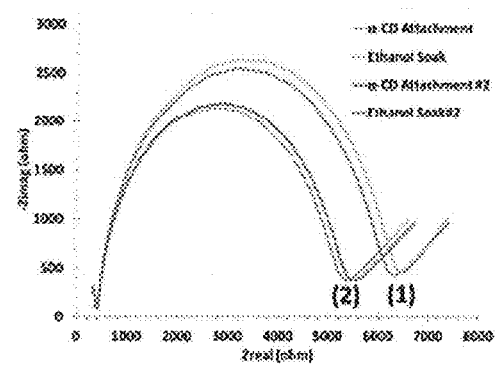
Figure 2C:
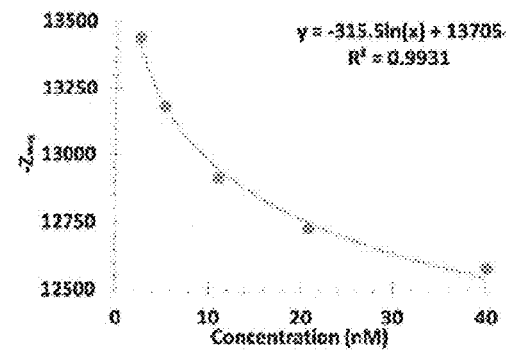

Using one or more rotaxanes may increase the sensitivity and/or range of an electrochemical sensor of the invention because of the increase of available surface bound supramolecules. A transition from FIG. 2A(1) to FIG. 2A(2) illustrates the loading of the electrochemical sensor's surface with cyclodextrin. A transition from FIG. 2A(2) to FIG. 2A(1) illustrates the unloading of cyclodextrin from the electrochemical sensor's surface. Surface coverage of the electrochemical sensor's surface with one or more rotaxanes may be adjusted for maximum repeatability and response to analytes. The surface may be calibrated to double layer capacitance change when exposed to analytes [as illustrated by a transition shown from FIG. 2A(2) to FIG. 2A(3)]. The graph shown in FIG. 2B illustrates the reloading shown in FIG. 2A(1) and FIG. 2A(2). The graph shown in FIG. 2C illustrates the detection of about 2.5 nM to about 40 nM cortisol. A rotaxane polymer sensor surface may be monitored with EIS and/or eQCM to observe the capability of the rotaxane polymer sensor surface to detect analyte.

By changing the crosslinking or terminal group of the poly-glycol surface, the antifouling capabilities of the surface may be altered. As a non-limiting example, poly(ε-caprolactone), which has both antifouling capabilities and the ability to form rotaxanes with cyclodextrin, may be used in embodiments of the invention.

In some aspects of the invention, an embodiment of an electrochemical sensor may be exposed to bovine serum albumin (BSA) prior to serial dilution. Because BSA is not hydrophobic and does not have an affinity to cyclodextrin, minimal disruption in the sensing paradigm is expected. Yet, BSA has the ability to disrupt detection by fouling the surface. A calibration curve in the presence and without the presence of BSA may be generated after multiple discharging/recharging of the cyclodextrin to determine fouling effects of the sensing paradigm.

Surface bound rotaxanes may have an increased range of detection because of the greater availability of cyclodextrin. With charging and discharging of the surface-bound cyclodextrin and antifouling polymers, the sensor surfaces may behave similarly in the presence of BSA as a clean buffered solution. Thus, the surfaces may perform adequately in complex systems, such as spiked plasma. In some instances and embodiments of the invention, the polymer end-group may be changed and/or the surface coverage of the polymer may be reduced to promote cyclodextrin interaction.

Although it has been found that strongest binding occurs with β-cyclodextrin, α-cyclodextrin has a smaller cavity than other cyclodextrin derivatives and therefore it can make inclusion complexes with a smaller range of hydrophobic molecules. Therefore, higher selectivity may be reached via α-cyclodextrin. Moreover, α-cyclodextrin is an appropriate receptor for determination of trans-resveratrol, which was used as a specific hydrophobic analyte in experiments described herein below. Resveratrol is a bioactive phytochemical produced in the skins of grapes and it exists in one of two isomeric forms, cis and trans. Although both forms display bioactivity, it is overwhelming found in grape skins in the trans form.

Art known experiments have been performed to produce a reusable biosensor by combination of self-assembled monolayers of PEG and cyclodextrin super molecules for detection of a hydrophobic analyte. These art known experiments show that metal electrodes can be coated by cyclodextrin without any additional support. Embodiments of the present invention, in contrast, modify the electrode sensor surface with PEG, PPG, or PBG prior to modification with cyclodextrin.

Certain experiments described herein below were performed to assess PEG:α-cyclodextrin. The experiments included serial dilution experiments carried out as set forth below. In these experiments the goal was to characterize the α-cyclodextrin and resveratrol interactions.

In contrast to cyclodextrin-adamantane complexed surfaces described herein, which exhibit a decreased impedance when cyclodextrin is removed from the surface, rotaxane modified surfaces exhibit an increased impedance when cyclodextrin is removed from the surface. This may be explained as follows. A PEG chain can exist in 2 different configurations. At low surface concentrations, there is no significant lateral interaction between terminally grafted chains, which exist in the mushroom configuration, whereas attached polymers exist in the brush configuration at high surface concentration. α-cyclodextrin threaded PEG chains may come together to form channel-type crystalline microdomains. So when there is no cyclodextrin on the PEG modified surface, PEG molecules have a mushroom configuration and are amorphous and, because of that, charge transfer resistance is higher. But, when cyclodextrin is loaded on the surface, PEG molecules become more oriented (crystalline) and charge transfer resistance becomes easier.

In general one expects an increase in charge transfer resistance with successive sensor modification steps that increase the biomolecular film thickness. This can be attributed to steric repulsion between a redox probe and carboxylate groups, which dramatically hinders electron transfer kinetics. When there is no cyclodextrin on PEG, PEG molecules are directly exposed to FFCN and the repulsion between FFCN and carboxylate groups of PEG hinders charge transfer. But when cyclodextrin is bound on top of PEG, carboxylate groups are covered and electron transfer is faster.

L-Glutamic Acid Modified Glassy Carbon Electrochemical Sensor Surface

In some embodiments of the invention, a sensor surface may be modified with L-glutamic acid. In certain embodiments of the invention, a sensor surface may be modified with L-glutamic acid as follows:
  (a) 50 mM L-glutamic acid may be prepared in 0.1 M PBS (pH=7). In certain embodiments of the invention, the 50 mM L-glutamic acid may be prepared by:
      a. adding about 0.7356 grams of L-glutamic acid to a flask;
      b. adding about 50 mL of 0.1 M PBS (pH=7) to the flask;
      c. stirring the mixture until dissolved using a sonicator; and
      d. adding another about 50 mL of 0.1 M PBS to being the total solution amount to 100 mL.
  (b) Polishing a glassy carbon electrode.
  (c) Filling a 20 mL beaker with 10 mL of the 50 mM L-glutamic acid/PBS solution.
  (d) Assembling the glassy carbon electrode and a reference electrode on a cross-flow style auxiliary electrode.
  (e) Performing electropolymerization a. Flow through the glassy carbon electrode with at least 750 uL UHP DI water then 750 uL 0.1M PBS to rinse the system (flow rate 100 uL/min); and
b. Conduct the electropolymerization using cyclic voltammetry.
  i. CV set up: −0.64 to +1.96V vs Ag/AgCl, 20 cycles, 100 mv/s
(f) Attach β-cyclodextrin on the poly-L-glutamic acid surface of the glassy carbon electrode.
  a. Flow through the glassy carbon electrode with 10 mM β-cyclodextrin in 0.1M PBS at flow rate of 200 uL/min for 30 min Poly-D-Lysine Modified Gold Electrochemical Sensor Surface In some embodiments of the invention, a sensor surface may be modified with D-lysine. In certain embodiments of the invention, a sensor surface may be modified with D-lysine as follows:
(a) Prepare 5 mM Dithiobis(succinimidyl propionate) (DTSP) in DMSO, 10 mM TCEP (tris (2-carboxyethyl) phosphine) in pH8.5 buffer solution.
(b) Clean a gold electrode surface.
(c) Cleave DTSP by TCEP.
  a. Mix 5 mL 5 mM DTSP/DMSO solution with 2.5 mL 10 mM TCEP solution above at room temperature for 10 min.
(d) Attach DTSP onto the gold electrode surface.
  a. Immerse the gold electrode surface within the above mixed solution for 30 min, then rinse with UHP.
(e) Attach poly-D-lysine on the gold electrode surface.
  a. Immerse the working electrode with 15 mL 0.1% poly-D-lysine aqueous solution overnight, then rinse with UHP.
(f) Bind α-cyclodextrin to the poly-D-lysine modified gold electrode surface.
  a. Flow through the modified gold electrode with 5 mM alpha-CD aqueous solution at flow rate of 200 uL/min for 30 min.

EIS Types

There are two major types of EIS that are currently used in electrochemical biosensors: faradaic and nonfaradaic. In faradaic EIS, addition of a redox probe such as $K_3Fe(CN)_6/K_4Fe(CN)_6$, that alternately oxidizes and reduces by transfer of an electron to and from the surface, is required and the charge transfer resistance is measured. In contrast, non-faradaic EIS is based on the change of electrical double layer properties of the electrode-electrolyte interface and, since no addition of any reagent is required, non-faradaic EIS may be more desirable for point of care applications. Besides, ferrocene can be included in the cavities of CD through a host-guest chemical reaction, thereby making faradaic EIS even less sensitive when it is used for analysis of sensors described herein. In this experiments described herein, faradaic EIS was chosen for monitoring the surface after each modification while non-faradaic EIS was employed to determine nm concentrations of analyte.

Adamantane-Bound Cyclodextrin Mediated Electrochemical Sensor Surface Experiments Experiments were performed that included certain embodiments of sensors and methods of the invention. Experiments, examples of which are described below, were used to assess various embodiments of electrochemical sensors capable of monitoring cyclodextrin binding of hydrophobic analytes. Certain initial experiments were control experiments performed prior to introducing modifications to the surface of the sensor used in the experiment.

Bare Sensor Surface Experiments

In one experiment, successive EIS runs were performed at different times of day, without altering the set up. FIG. 3A illustrates Nyquist plots of successive runs of EIS without altering setup at different times of day. FIG. 3A-D illustrates control experiments conducted prior to modification of a sensor surface. The corresponding graphs FIG. 3B and FIG. 3D below the Nyquist plots (FIG. 3A and FIG. 3C, respectively), compare the Rct behavior with the run at which it was observed. While the difference is slight, it can be observed that conducting experiments in the afternoon may prevent nonspecific Rct changes. Abbreviations used in FIGS. 3-12 and elsewhere herein are as follows: Rct=charge transfer resistance, Zimag=imaginary or out of phase version of the impedance, and Zreal=real or in phase version of the impedance.

Experiments were carried out in which a decrease in concentration was tested by performing a reverse serial dilution from high concentration to lower concentration. It was determined that success of such reverse serial dilution testing was likely dependent on reloading of β-cyclodextrin on the surface bound adamantane. Experiments were performed in which the surface-bound adamantane was reloaded with cyclodextrin.

Figures 4A, 4B, 4C, 4D:
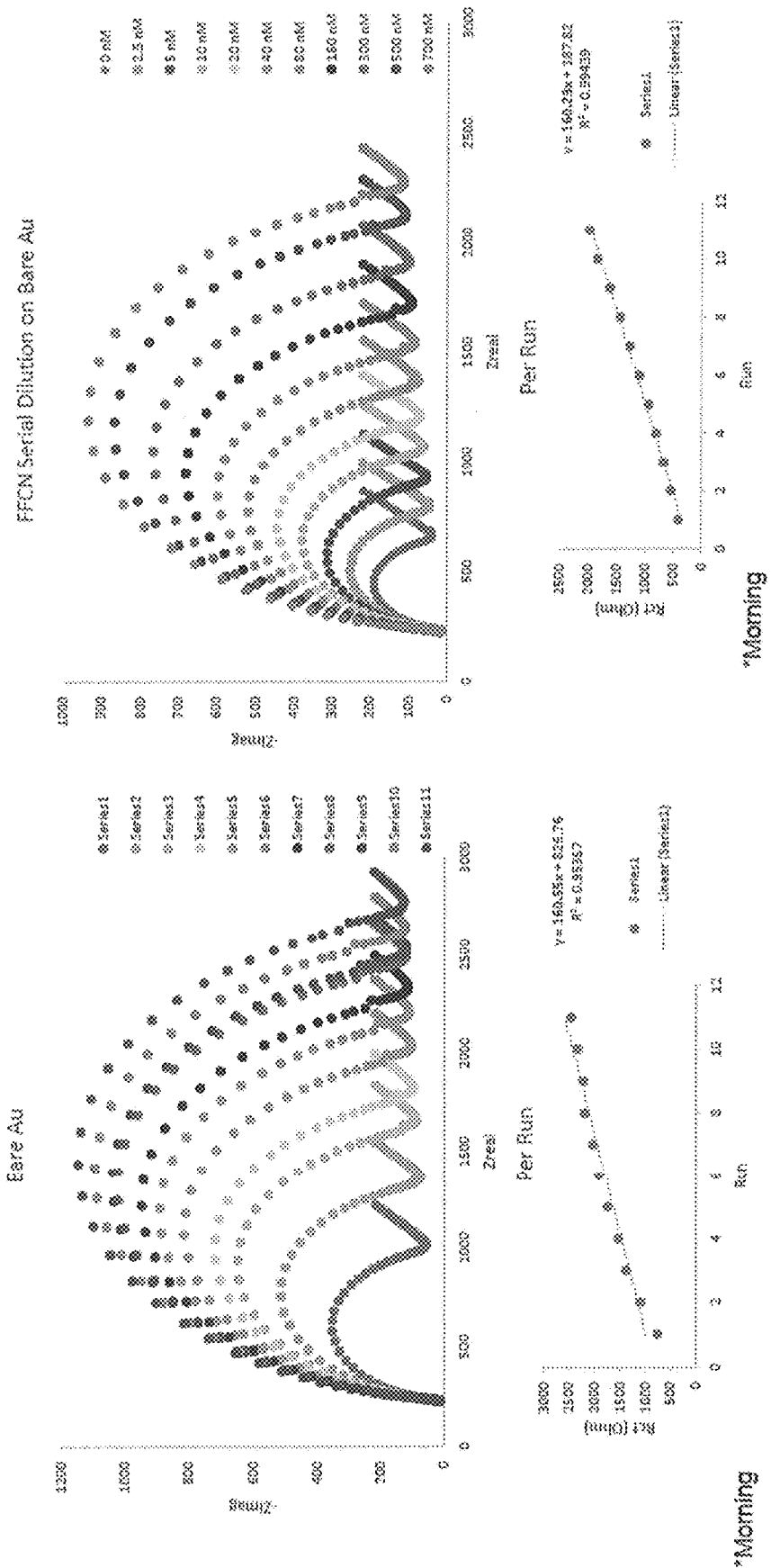
FIG. 4A-D illustrates a $Fe(CN)_6^{3-/4-}$ serial dilution as a control experiment conducted prior to modification of a sensor surface according to certain embodiments of the present disclosure.

Results from one experiment are shown in FIG. 4A-D, which illustrates a $Fe(CN)_6^{3-/4-}$ (FFCN) serial dilution as compared to a control experiment conducted prior to modification of a sensor surface. The FIGS. 4A and 4B is identical to the "Bare Au-Morning" portion of FIGS. 3C and 3D. The FIG. 4C, labeled "FFCN Serial Dilution on Bare Au," represents a control serial dilution mimicking a serial dilution containing an analyte of interest. The analyte was left out in order to determine if the addition of volume contributed to nonspecific Rct patterns. FIG. 4B and FIG. 4D correspond to FIG. 4A and FIG. 4C, respectively. The slopes provided in the FIG. 4B and FIG. 4D graphs show that that the linear pattern of Rct increase of "Bare Au" is nearly identical to that of "FFCN Serial Dilution on Bare Au," indicating no additional Rct changes are caused by volume addition.

Results of another serial dilution experiment are provided in FIG. 5A-D, which illustrates the FFCN serial dilution of FIG. 4A-D as compared to a hydrocortisone serial dilution. FIG. 5A is identical to the "FFCN Serial Dilution on Bare Au" plot of FIG. 4C. The FIG. 5B graph was altered from the FIG. 4D graph to compare Rct patterns with mimicked analyte concentrations in order to compare slopes with the serial dilution, represented in FIGS. 5C and 5D. The serial dilution included addition of hydrocortisone from a stock solution to the analyte solution used for conducting EIS. Thus, the addition of the solution lead to an increase in analyte concentration. Concentrations are provided in the Nyquist plot in the FIG. 5C, which represents a hydrocortisone serial dilution on a bare Au electrode. While the results indicate a smaller slope than that of the FFCN serial dilution, the line of fit was not suitable.

Adamantane Modified Sensor Surface Experiments

In certain experiments, adamantane was attached to a gold (Au) electrode by a thiol self-assembled monolayer with a tris(2-carboxyethyl)phosphine (TCEP) reducing agent (as illustrated in section 2 of FIG. 1) using the following methodology.
(a) A mixture of about 20 mM to about 40 mM adamantane-thiol was prepared in 0.35 mM TCEP and DMSO/ethanol.

(b) A polished Au electrode was contacted with the adamantane-thiol mixture for times that ranged from about 16 hours to about 24 hours.

(c) After contacting, the Au electrode was rinsed with DMSO, methanol, ethanol, chloroform, dimethylformamide (DMF), tetrahydrofuran (THF), or another organic solvent.

(d) Option (i): the resulting rinsed Au electrode was sonicated.

Option (ii): the resulting rinsed Au electrode was not sonicated.

Note: it was identified that the sonicating could damage attachment of the monolayer to the electrode and therefore certain experiments included (d) Option (ii) instead of (d) Option (i).

Experiments were performed in which different solvents were used in the attachment process. FIG. 9A-B illustrates a comparison of thiol attachments in different solvents with identical preparation and treatment procedures according to embodiments of the present disclosure. FIG. 9A shows a response when dimethyl sulfoxide was used and FIG. 9B shows a response when 200-proof ethanol was used. While only one plot is illustrated for an ethanol trial, further experiments proved ethanol provided a more consistent response.

Adamantane-Bound Cyclodextrin Mediated Electrochemical Sensor Surface Experiments In certain experiments, a cyclodextrin:adamantane complexed surface was used. In certain experiments an adamantane-modified surface of an electrochemical sensor was exposed to β-cyclodextrin to form a β-cyclodextrin:adamantane surface complex. In certain experiments, a β-cyclodextrin solution of about 10 mM to about 15 mM was created. In certain experiments, the β-cyclodextrin solution may be created in phosphate-buffered saline (PBS). In certain experiments, the Au electrode with the adamantane-modified surface was contacted with the β-cyclodextrin solution from about 10 minutes through over 1.5 hours, resulting in a β-cyclodextrin:adamantane surface complex having a 1:1 relationship. In other words, one β-cyclodextrin may interact with one surface bound adamantane.

The β-cyclodextrin may have various functional groups. It was identified that the β-cyclodextrin could be removed from the β-cyclodextrin:adamantane surface complex in the presence of hydrophobic content. The β-cyclodextrin could also be removed from the β-cyclodextrin:adamantane surface complex by contacting (e.g., rinsing) the surface with dimethyl sulfoxide (DMSO), methanol, ethanol, chloroform, dimethylformamide (DMF), tetrahydrofuran (THF), or another organic solvent. The organic solvents disrupted the β-cyclodextrin:adamantane affinity (i.e., disrupted non-covalent bonding of the β-cyclodextrin:adamantane surface).

Figures 6A, 6B, 6C:
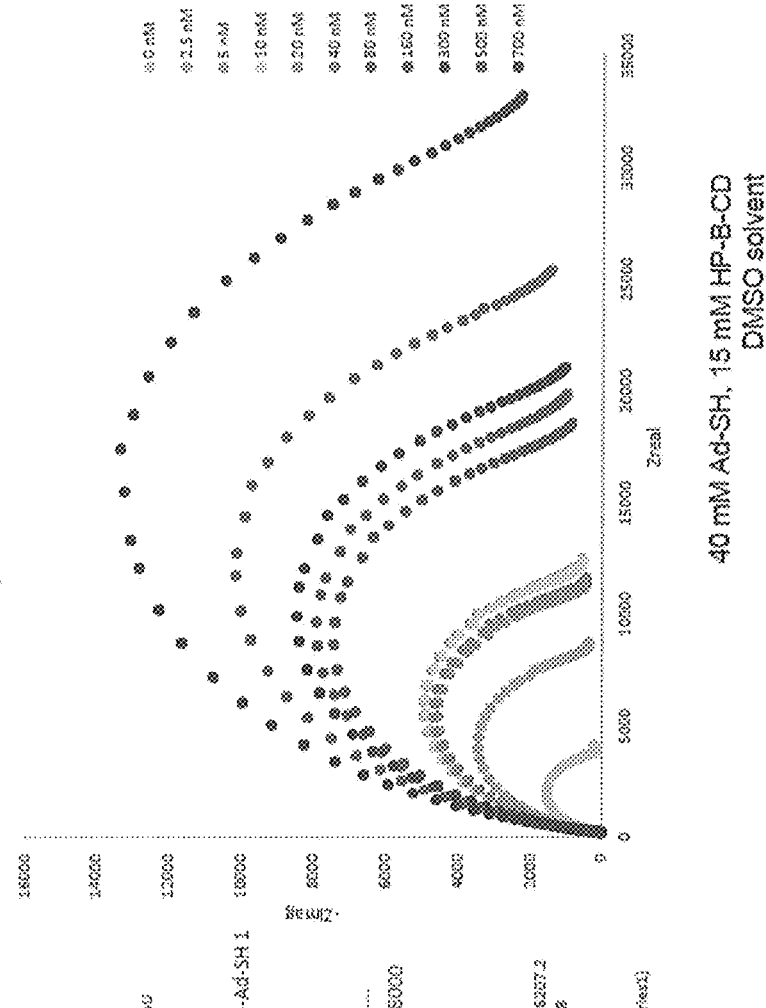
FIG. 6A-C illustrates a Nyquist plot monitoring an adamantane-hydroxypropyl-β-cyclodextrin attachment, a hydrocortisone serial dilution using this modification, and a graph for the serial dilution relating Rct to analyte concentration. The attachment plot (FIG. 6A) shows significant Rct increase with each modification, as more molecular layers are being deposited on the surface, thereby impeding electron flow. However, the serial dilution plot (FIG. 6B) and graph (FIG. 6C) show an increase in Rct pattern with each serial dilution, which is contradictory to the theorized response.

FIG. 6A illustrates a Nyquist plot monitoring an adamantane-hydroxypropyl-β-cyclodextrin attachment. FIG. 6B shows a hydrocortisone serial dilution using this modification, and FIG. 6C shows a graph for the serial dilution relating Rct to analyte concentration. The attachment plot shows significant Rct increase with each modification, as more molecular layers are being deposited on the surface, thereby impeding electron flow. However, the serial dilution plot and graph shows an increase in Rct pattern with each serial dilution, which is contradictory to the theorized response.

FIG. 7A-C illustrates a second attempt at the attachment and serial dilution, showing similar behaviors as represented in FIG. 6A-C. FIG. 7A shows a Nyquist plot monitoring an adamantane-β-cyclodextrin attachment. FIG. 7C shows a hydrocortisone serial dilution using this modification, and FIG. 7B shows a graph for the serial dilution relating Rct to analyte concentration according to embodiments of the invention.

Figures 8A, 8B, 8C:
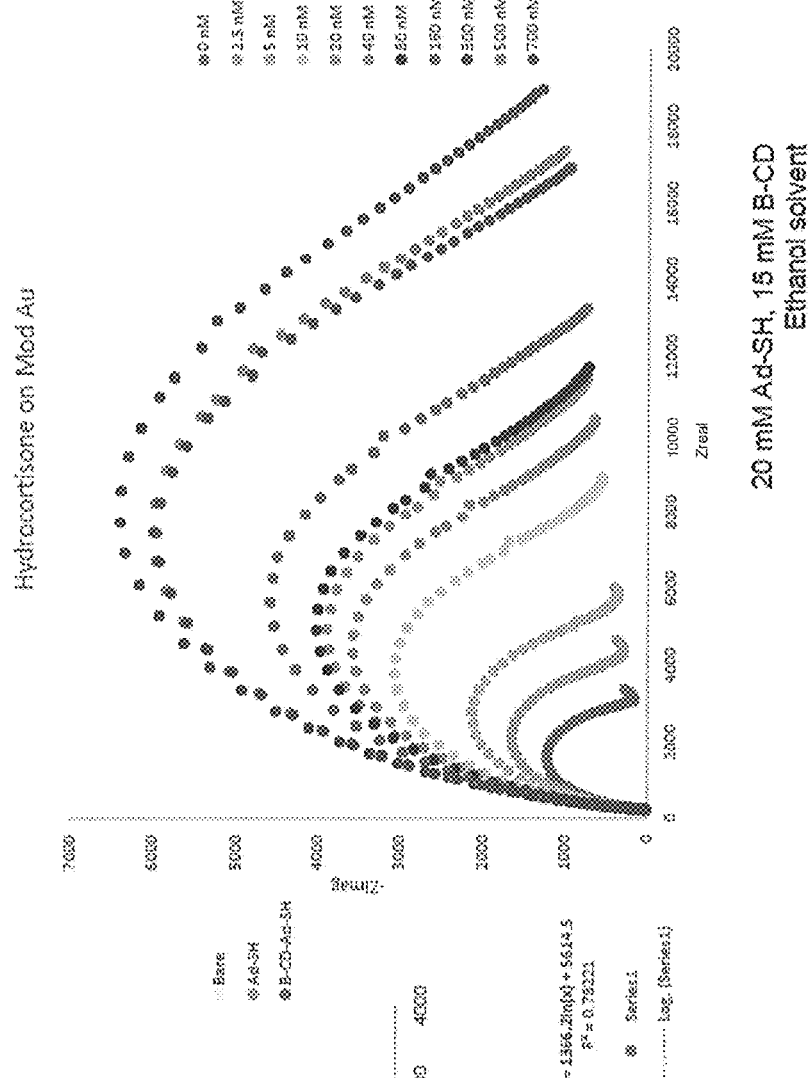
FIG. 8A-C illustrates two different attempts at attaching adamantane to a gold (Au) surface of a sensor via a gold-thiol covalent bond according to certain embodiments of the present disclosure. Two different patterns were observed when completing this procedure.

FIG. 8A-C shows results of two different attempts of attaching adamantane to an Au surface of a sensor via an Au-thiol covalent bond. Two different patterns were observed when completing this procedure. The FIG. 8A-B represents an expected Rct increase coupling the thiol attachment. Rct significantly decreases to a value less than that achieved when the electrode was bare. This made it difficult to determine whether the attachment was successful.

Figure 10:
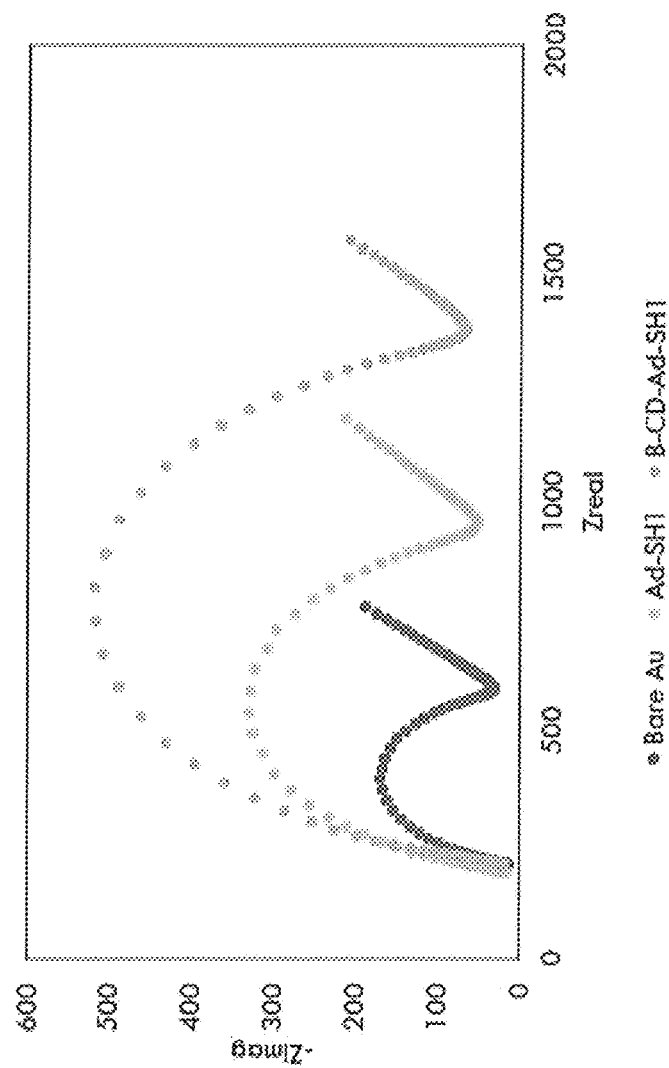
FIG. 10 illustrates an example of a modified electrode and its Rct response according to certain embodiments of the present disclosure.
Figure 11:
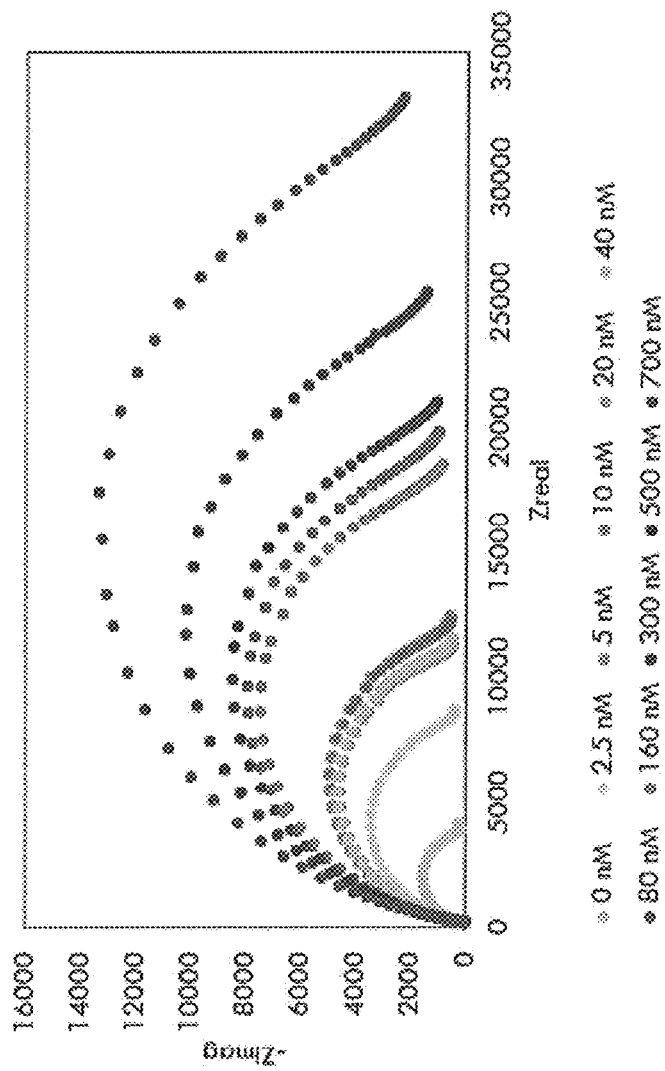
FIG. 11 illustrates an example of a serial dilution of hydrocortisone on the modified electrode of FIG. 10 according to certain embodiments of the present disclosure.

FIG. 10 illustrates an example of a modified electrode and its Rct response. The electrode was modified with adamantane-β-cyclodextrin self-assemblies. FIG. 11 illustrates an example of a serial dilution of hydrocortisone on the modified electrode of FIG. 10.

Reloading of Adamantane-Bound Cyclodextrin Mediated Electrochemical Sensor Surface Experiments Experiments were carried out to examine the reloading and rinsing of modified sensor surfaces. In certain experiments, a modified sensor surface (post-release of cyclodextrin) was rinsed in ethanol and UHP, then soaked in ethanol for 30 minutes, then rinsed again in ethanol and UHP, and then placed in β-cyclodextrin solution for 30-45 minutes, which was followed by a quick UHP rinse prior to EIS testing. Results of reloading of the sensors indicated the reloading was beneficial compared to use of previously known sensors, some of which required abrasive removal and reapplication of surface modifications in order for the sensor to be used again. Experiments confirmed that sensors prepared and used as set forth herein were able to be reused simply by reloading cyclodextrin, at least in part, because the cyclodextrin was a secondary modification of the sensor surface.

Figure 12:
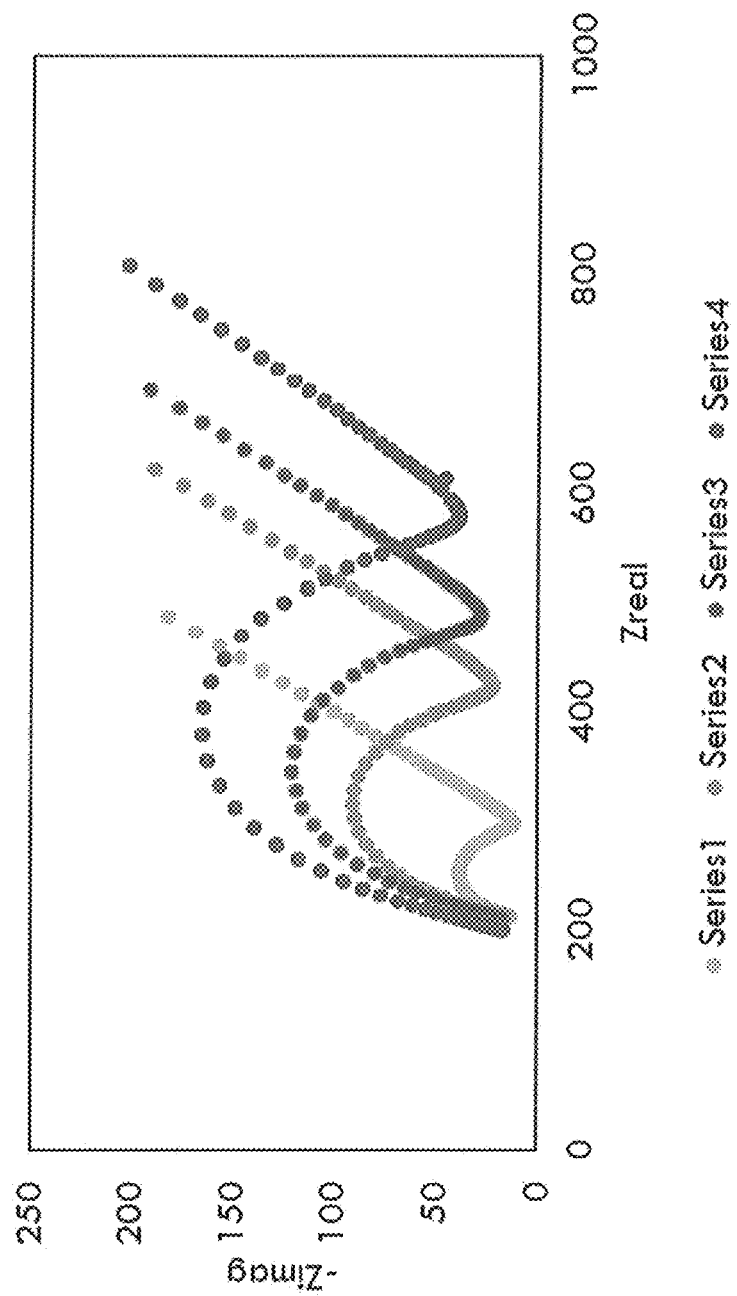
FIG. 12 illustrates reproducibility issues observed with EIS according to certain embodiments of the present disclosure.

Results of a reproducibility experiment are shown in FIG. 12, which illustrates reproducibility issues observed with EIS. The Nyquist plot of FIG. 12 shows Rct increases after 4 successive runs of EIS that occur due to the absence of electrode cleaning between each run. This was significant because a modified electrode can no longer be cleaned in the same manner as a bare electrode. Thus, assessing the response when an electrode cannot be cleaned is significant in defining Rct behaviors nonspecific to the modification or analyte detection.

It was identified that an initially large, predictable, and repeatable surface impedance could be expected after each reloading of β-cyclodextrin. If the impedance didn't return to predictable levels after reloading, surface characterization could be performed to determine inconsistencies. Using EIS and eQCM, an optimal contact time of the β-cyclodextrin solution with the adamantane-sensor surface could be determined.

Discussion

Experiments were performed to assess adding a hydroxypropyl group to β-cyclodextrin to identify whether this resulted in changes in the binding rates of β-cyclodextrin to cortisol, see for example, FIGS. 6 and 7, which provide results from use of aβ-cyclodextrin derivative in an embodiment of a sensor of the invention. Experiments were performed and their results demonstrated that the electrochemical sensor of the invention was able to produce repeatable and reproducible signals. This conclusion was supported by the multiple serial dilution calibration curves and control experiments that were completed. The electrochemical sensor was able to produce the same baseline and predictable analyte response without the need to polish or re-modify the surface of the electrochemical sensor. A different impedance response was observed for each analyte and each supramolecule tested.

Rotaxane Electrochemical Sensor Surface Experiments

Experiments were performed to assess various embodiments of electrochemical sensors that include rotaxane electrochemical sensor surfaces. Fouling (e.g., the accumulation of unwanted material on the sensor surface) may arise in complex biofluid matrices. When fouling occurs, rinsing the electrochemical sensor with DMSO and ethanol may not be sufficient for deterring biofilm formation. Antimicrobial surfaces may be used to deter biofilm formation as well as a supramolecular mediated sensor surface.

Using a polymer-brush self-assembled monolayer, one or more rotaxanes of surface bound cyclodextrin were achieved. It was identified that sensors with one or more rotaxanes of surface bound cyclodextrin had an increased range of the sensor and/or resulted in reduced fouling of the sensor surface used in detection of hydrophobic analytes. As described elsewhere herein, a rotaxane is an assembly with multiple supramolecules trapping a linear self-assembled polymer chain. Because multiple cyclodextrins could be added to a sensor surface, the range of the sensor could be increased using one or more rotaxanes.

In certain experiments, a surface was modified with about 500 MW polyethylene glycol (PEG) via thiol gold interaction [as illustrated in FIG. 2A(1)]. The modified surface was contacted with an α-cyclodextrin solution to form one or more surface bound rotaxanes [as illustrated in FIG. 2A(2)]. It was identified that use of one or more rotaxanes increased the sensitivity and/or range of an electrochemical sensor of the invention because of the increase of available surface bound supramolecules.

Results shown in the graph in FIG. 2C illustrate the detection of about 2.5 nM to about 40 nM cortisol. Experiments indicated that a rotaxane polymer sensor surface could be monitored with EIS and/or eQCM to observe the capability of the rotaxane polymer sensor surface to detect analyte. Experiments indicated that antifouling capabilities of the surface could be altered by changing the crosslinking or terminal group of the poly-glycol surface.

Preparing PEG:α-Cyclodextrin Modified Sensor Surfaces

In certain experiments, PEG:α-cyclodextrin modified sensor surface was prepared and tested as follows:

(a) The electrode was polished.

(b) A background signal was obtained with 20 mM Ferri/ferrocyanide in ultra-high purity water (DI water at 18.2 MΩ).

(c) The electrode surface was modified with a thiol activated group (although other types of modifications can be used). For PEG, the surface modification was performed using a HS-PEG$_{12}$-CT(carboxylate) at 0.5 mg/mL. The modification took 45 minutes in UHP.

(d) An EIS signal with 20 mM Ferri/ferrocyanide in ultra-high purity (UHP) water (DI water at 18.2 MΩ) was taken.

(e) The surface was exposed to cyclodextrin in UHP or PBS or another aqueous buffer. Certain experiments used 20 mM cyclodextrin with a 30 min soak and water rinse.

(f) An EIS signal with 20 mM Ferri/ferrocyanide in ultra-high purity (UHP) water (DI water at 18.2 MΩ) was taken.

(g) After Step (f), the electrode surface was exposed to different concentrations of an analyte (e.g., resveratrol), and an EIS signal was taken in Ferri/ferrocyanide or directly in buffer.

Figure 13:
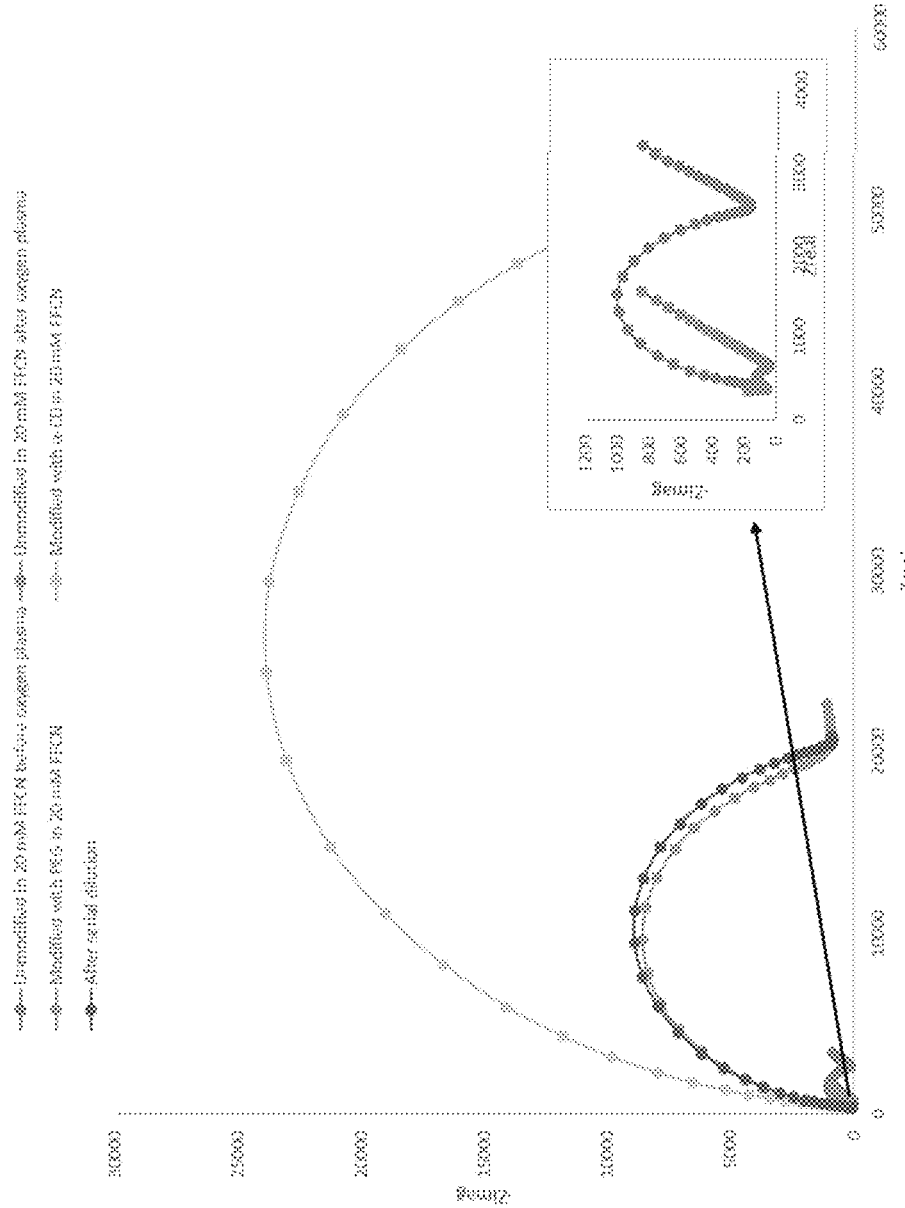
FIG. 13 illustrates attachment of polyethylene glycol (PEG) and α-cyclodextrin to a sensor surface according to certain embodiments of the present disclosure.
Figure 14:
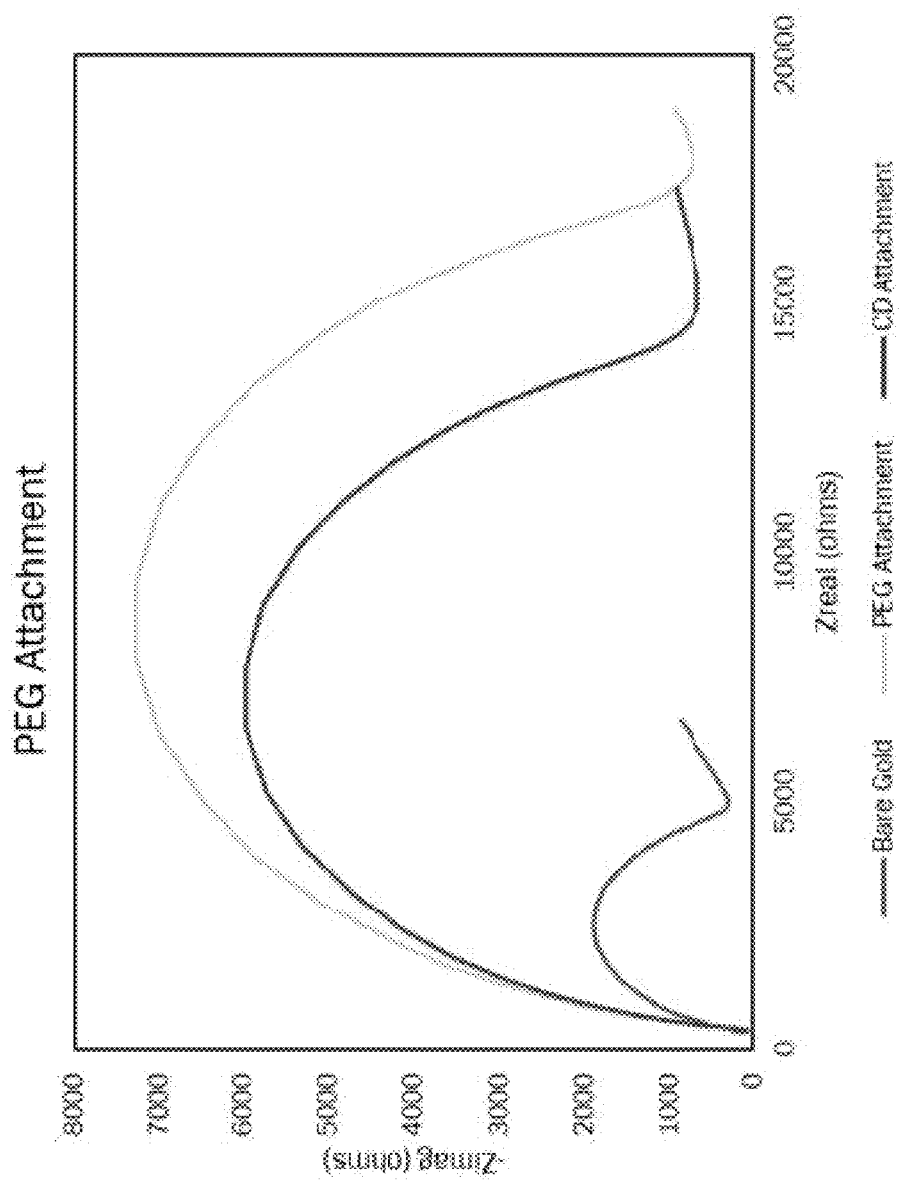
FIG. 14 illustrates attachment of polyethylene glycol (PEG) and α-cyclodextrin to a sensor surface according to certain embodiments of the present disclosure.
Figure 15:
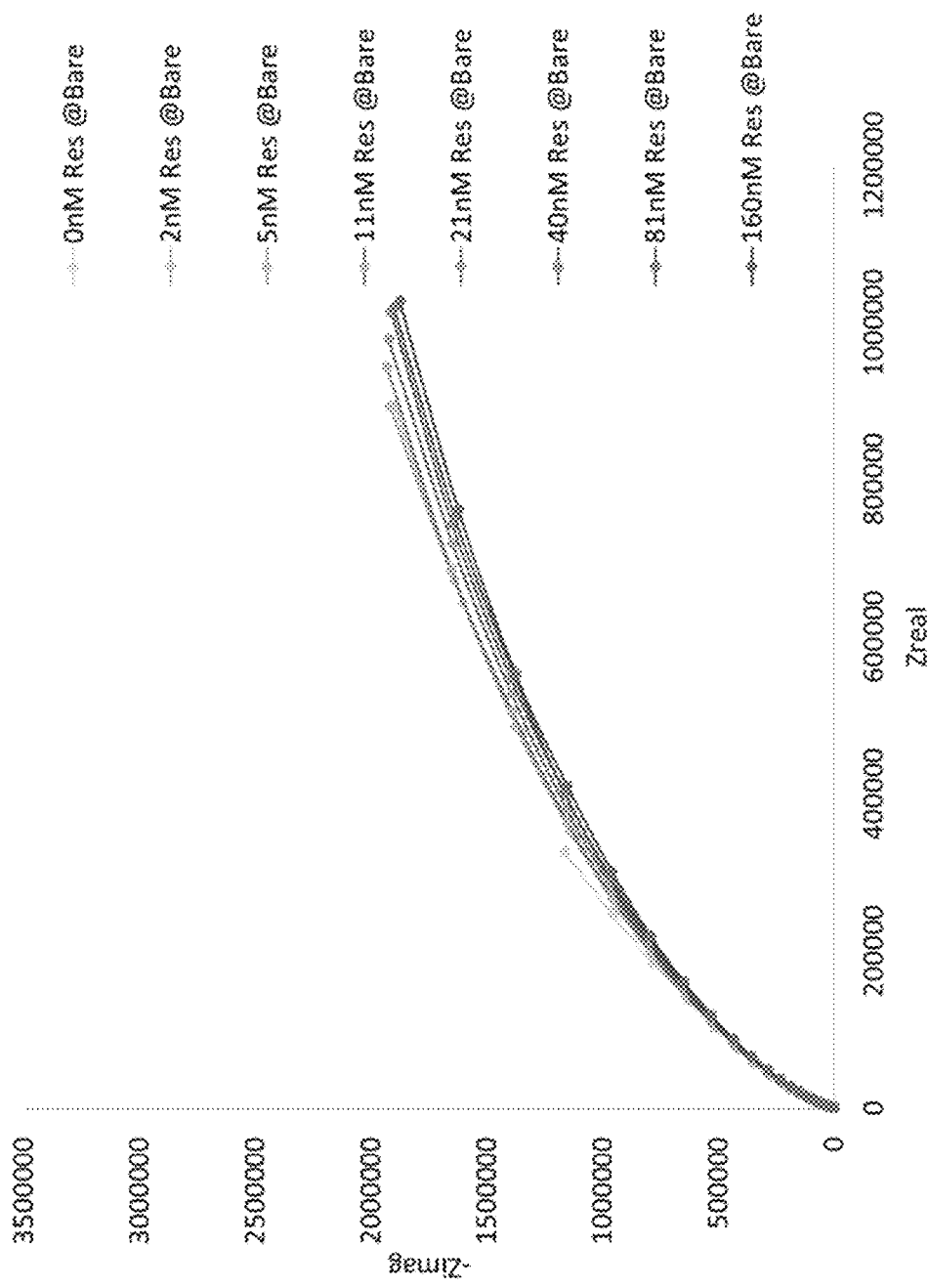
FIG. 15 illustrates an EIS serial dilution of resveratrol with a bare electrode surface according to certain embodiments of the present disclosure.
Figure 16:
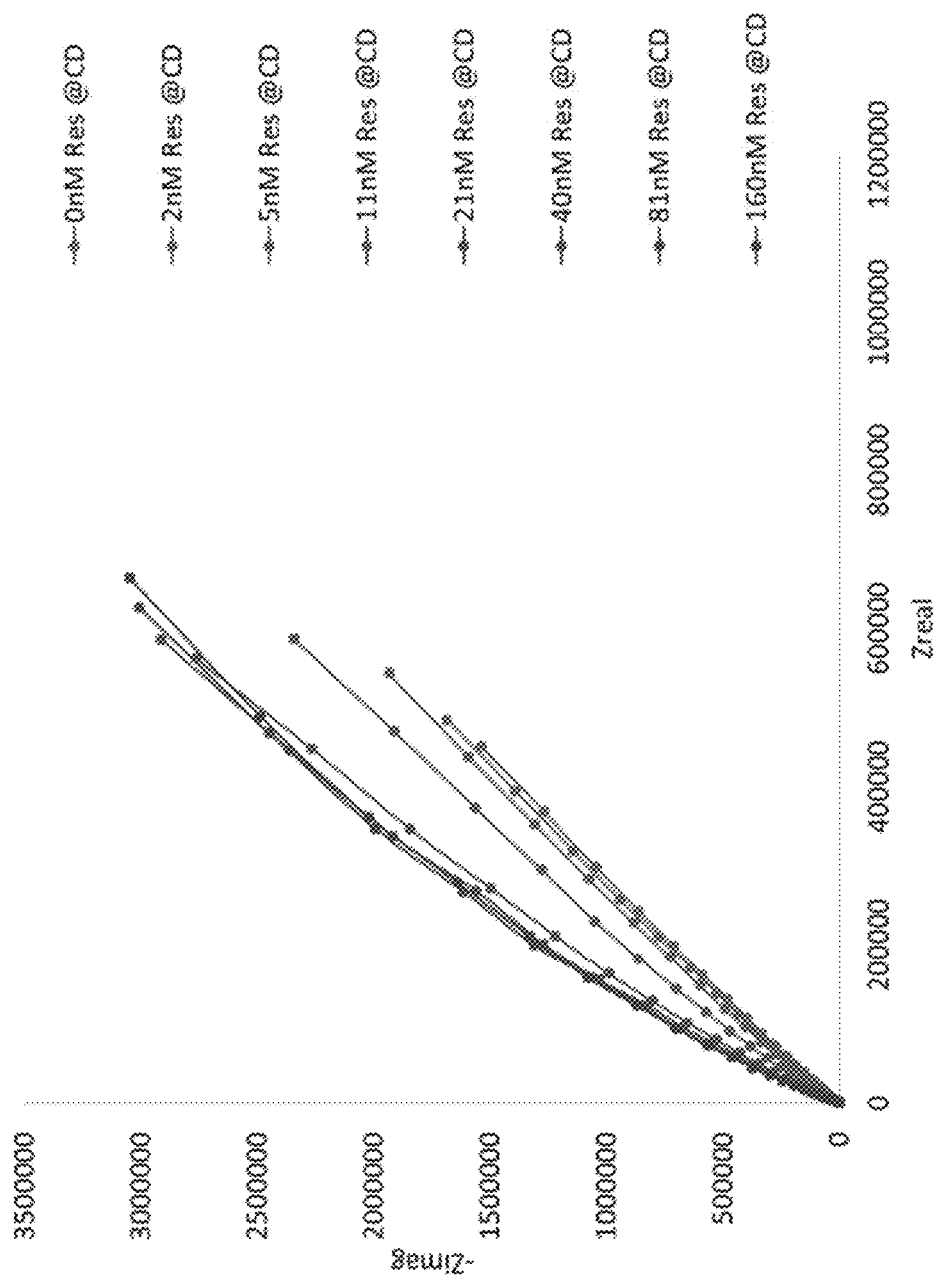
FIG. 16 illustrates an EIS serial dilution of resveratrol with a PEG:α-cyclodextrin modified sensor surface according to certain embodiments of the present disclosure.
Figure 17:
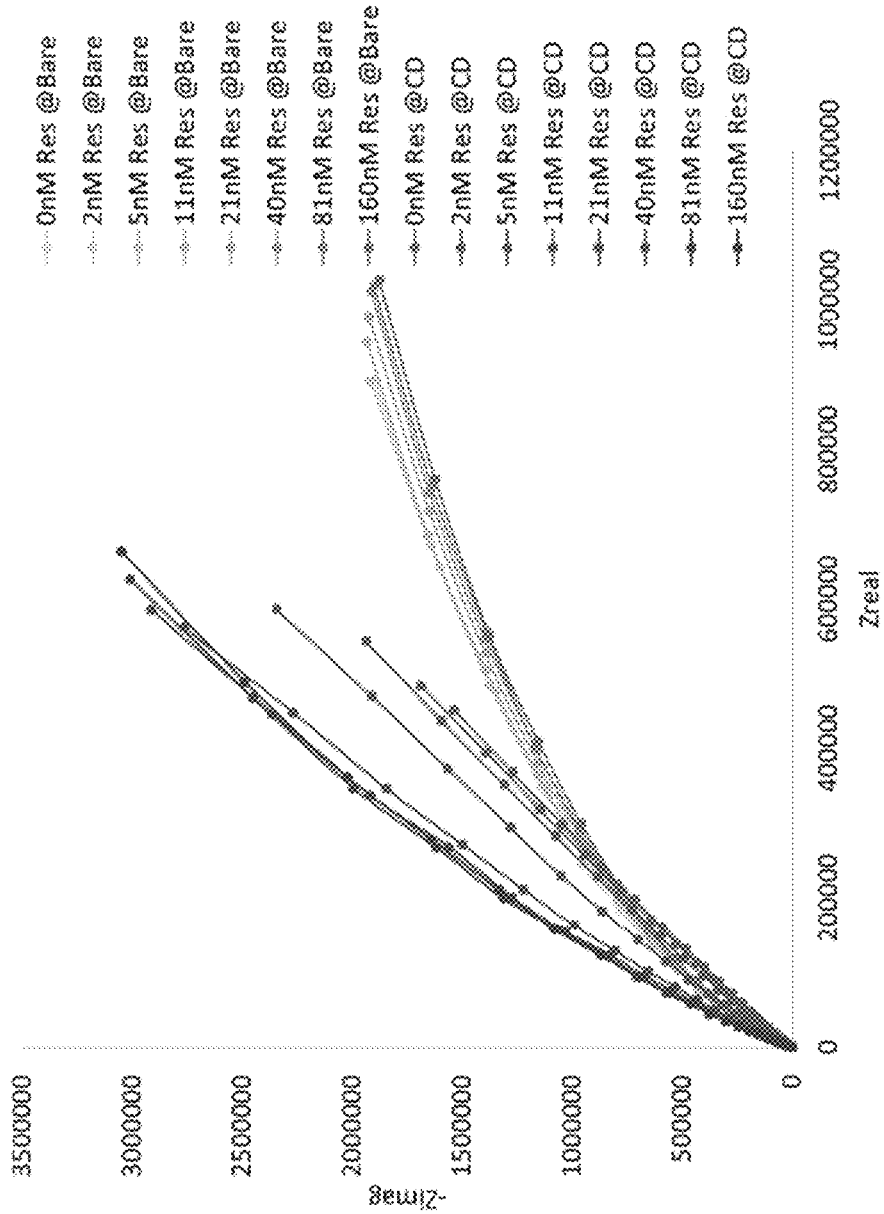
FIG. 17 illustrates a comparison of results of EIS serial dilutions of different sensor surfaces according to certain embodiments of the present disclosure.
Figure 18:
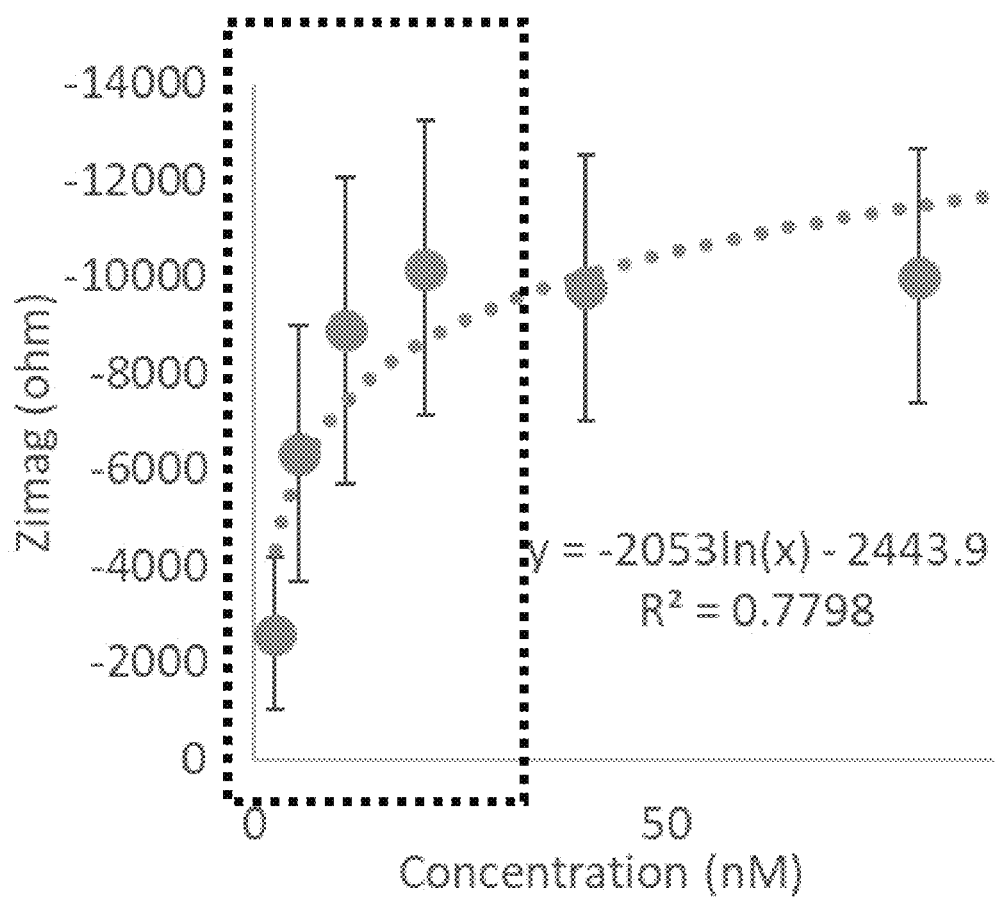
FIG. 18 provides a graph comparing concentration versus Zimag. The results illustrate trends in how the signal changed as concentration of resveratrol increased, indicating a cyclodextrin release from the surface. N=6.
Figure 19A:
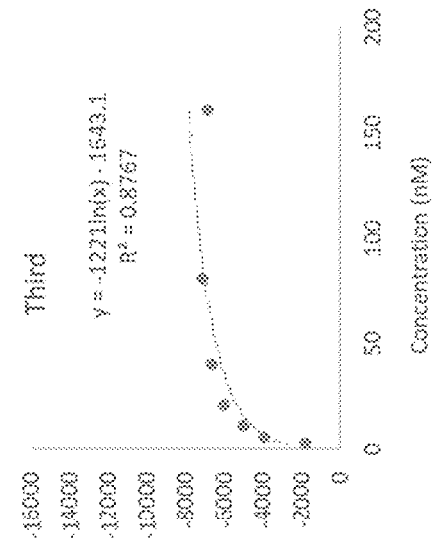
FIG. 19A-F provides graphs of results of the serial dilution relating Rct to analyte concentration for each individual electrode indicated in FIG. 18.
Figure 19B:
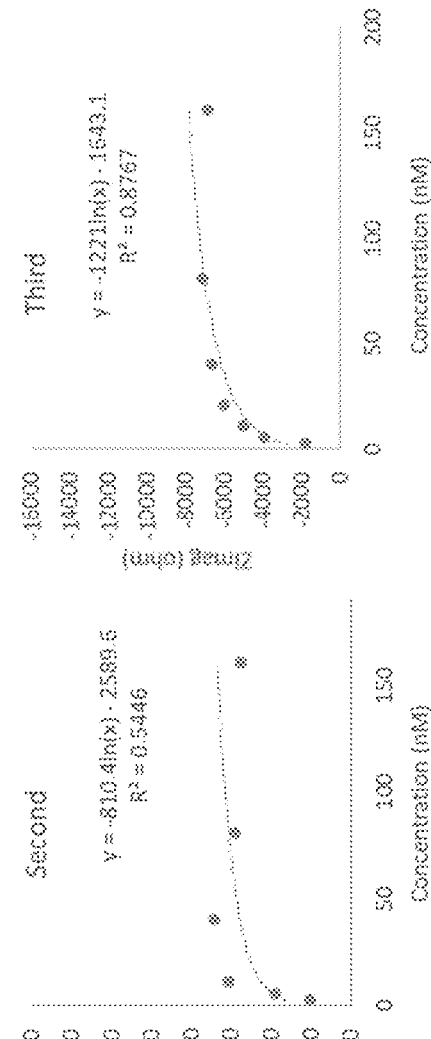
Figure 19C:
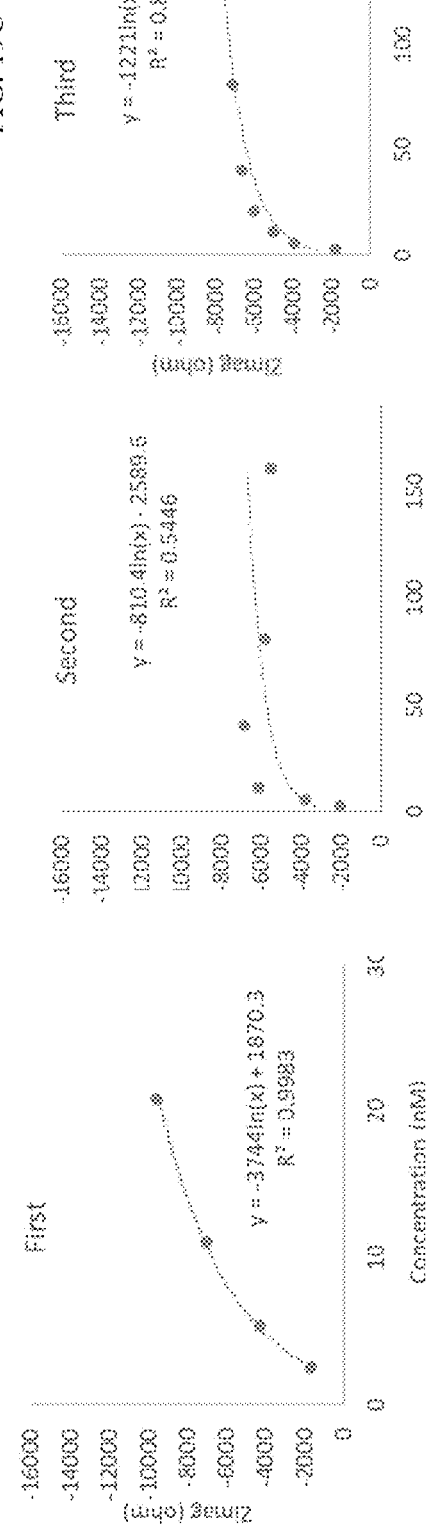
Figure 19D:
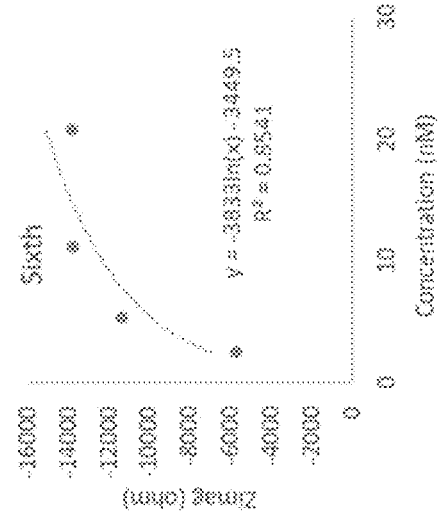
Figure 19E:
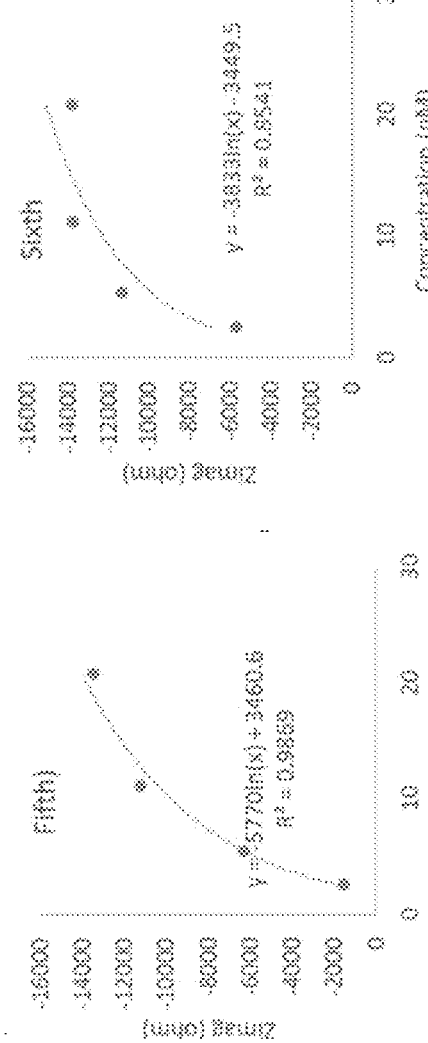
Figure 19F:
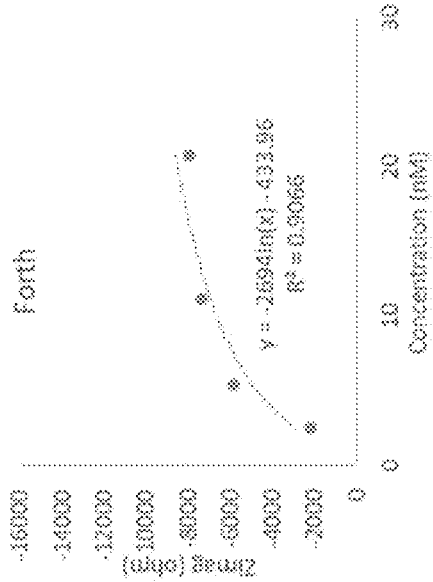
Figure 20A:
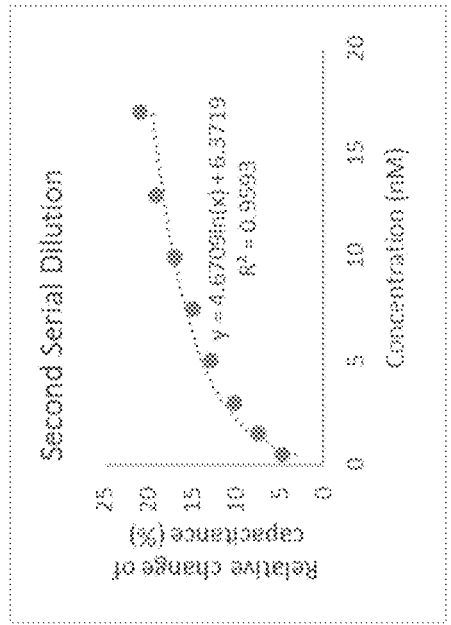
FIG. 20A-C provides graphs of concentration versus relative capacitive change of a single electrode showing a reusability of the sensor towards resveratrol sensing.
Figure 20B:
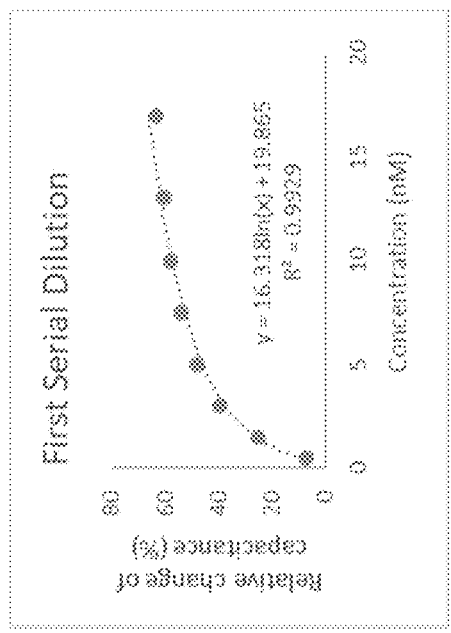
Figure 20C:
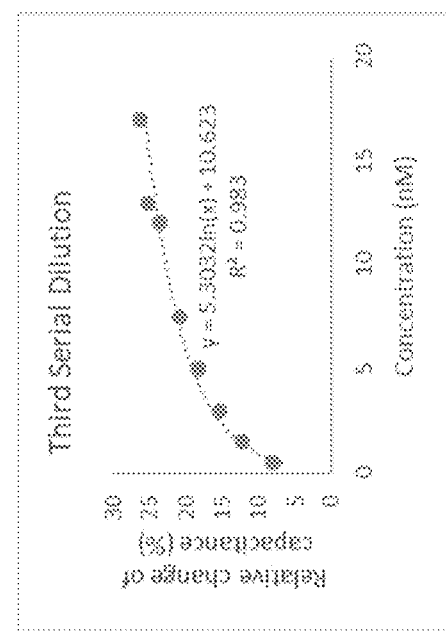
Figure 21A:
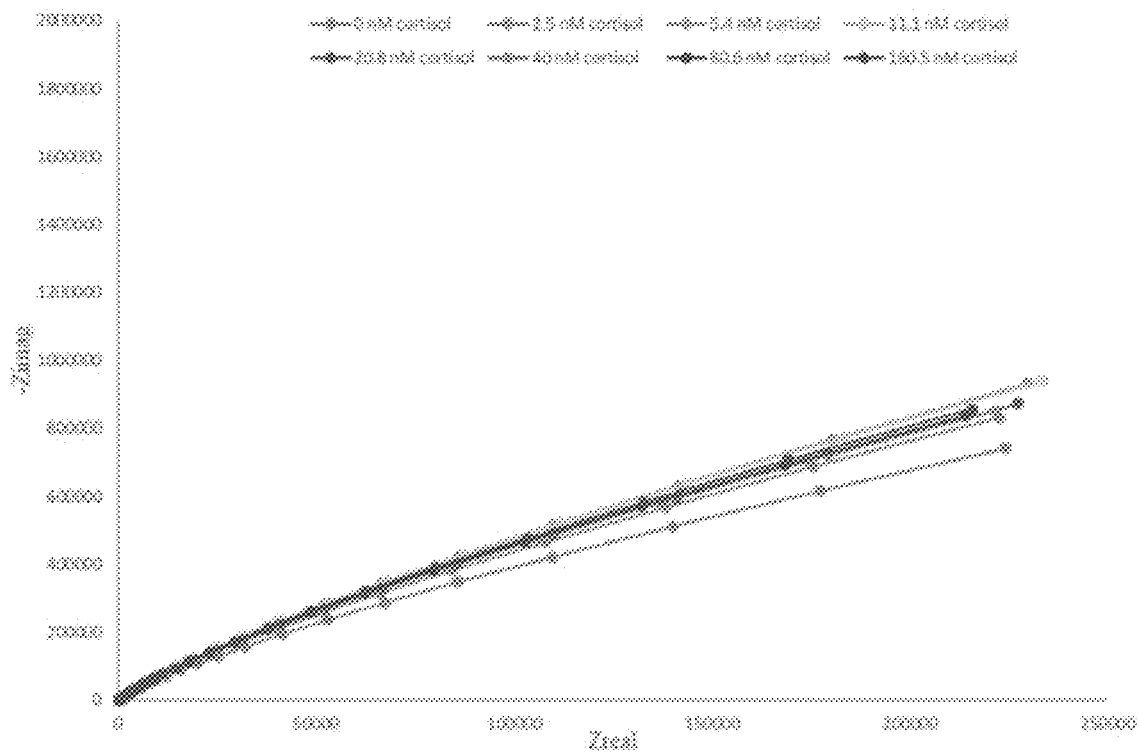
FIG. 21A-B shows when the sensor was exposed to cortisol instead of being exposed to resveratrol. Because cortisol does not complex with α-cyclodextrin, no signal is observed in FIG. 21A.
Figure 21B:
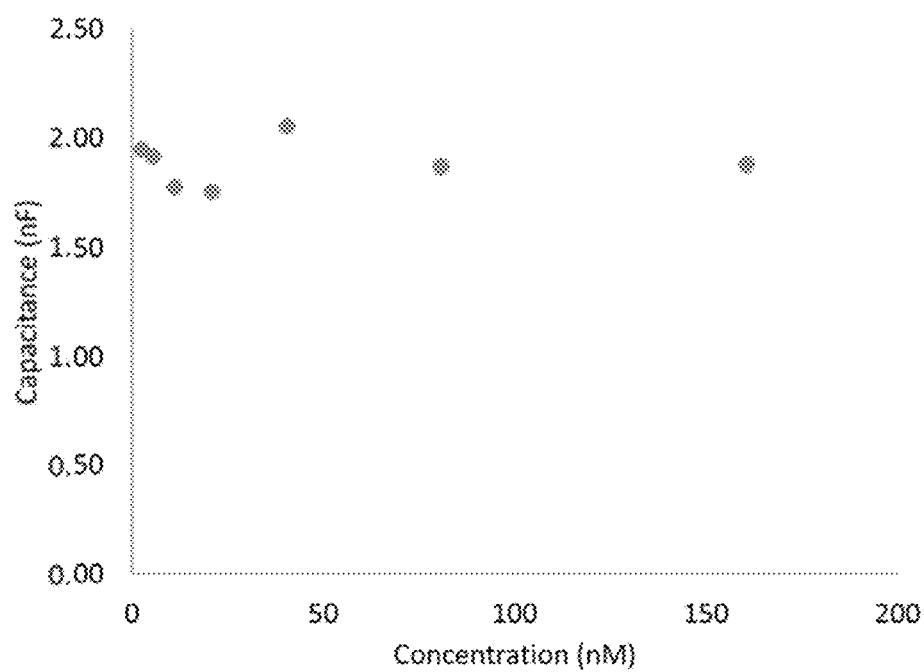
Figure 22C:
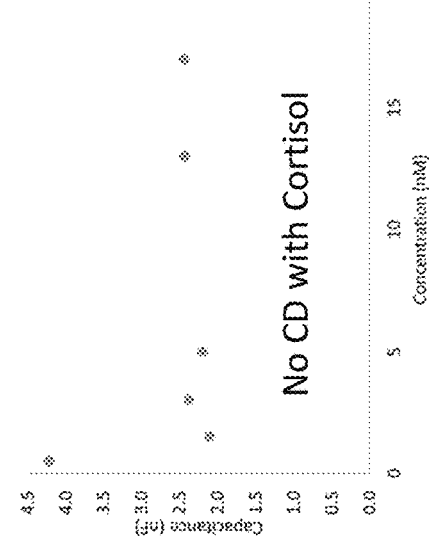
FIG. 22A-D provides graphs of concentration versus relative capacitive change for various sensor controls indicating the response of the α-cyclodextrin is specific to only molecules complexed with it.
Figure 22D:
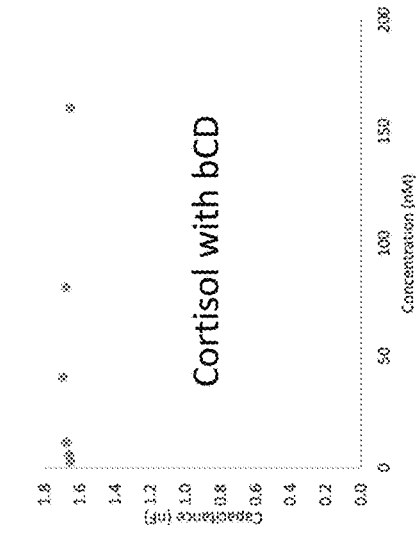
Figure 22A:
Figure 22B:
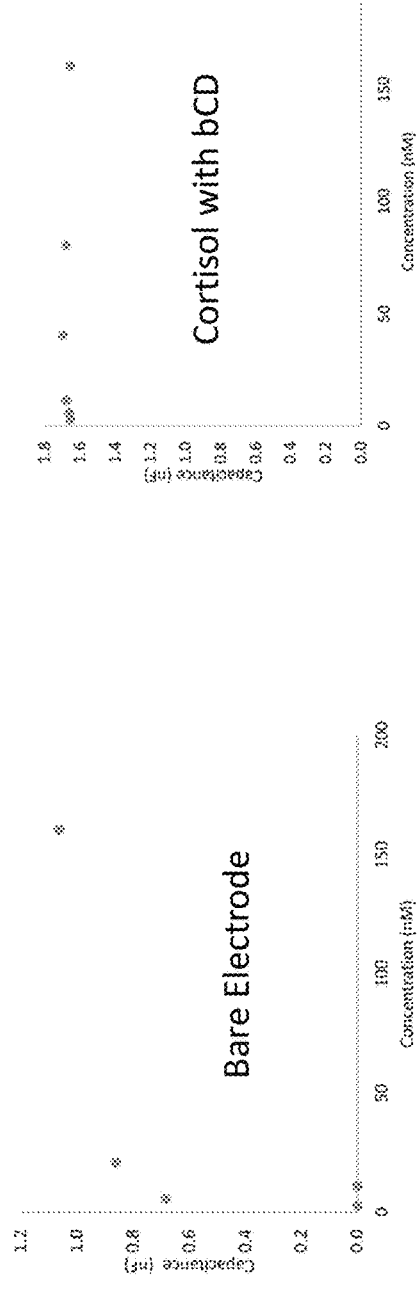
Figure 23:
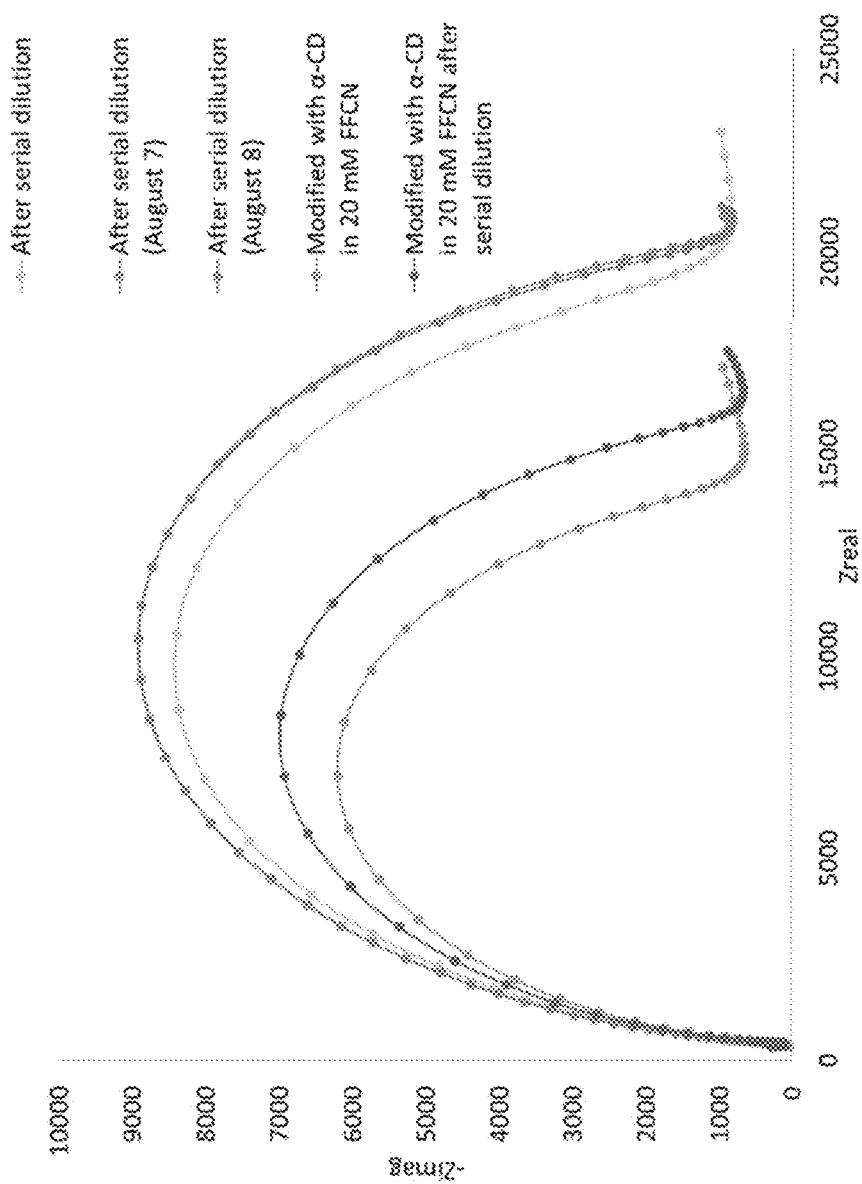
FIG. 23 provides a graph showing the reproducibility for the surface after/before each serial dilution demonstrated in FIG. 20A-C.
Figures 24A, 24B:
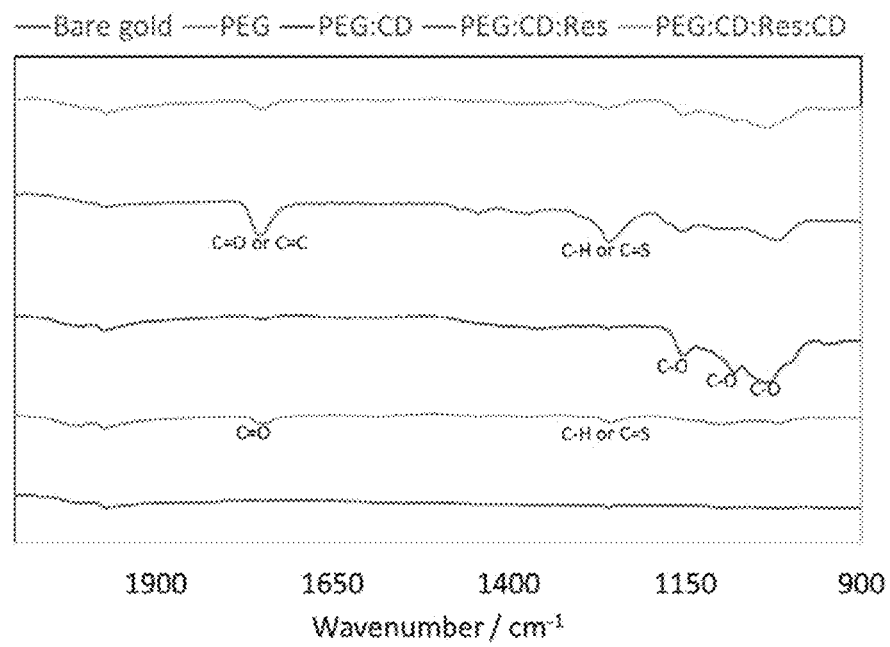
FIG. 24A-B shows traces and a table.
Figure 25:
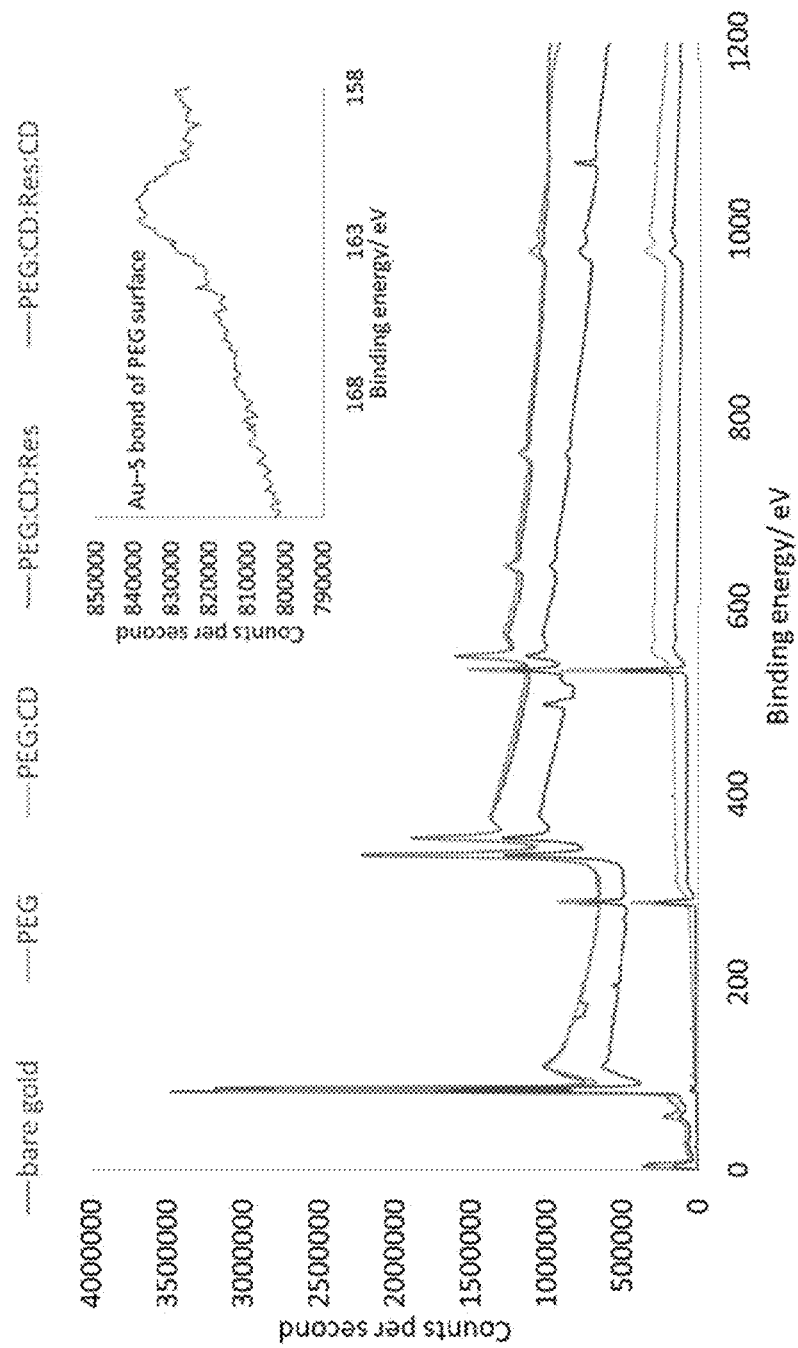
FIG. 25 provides a graph showing XPS signal confirming that cyclodextrin is being removed from the surface and added to the surface.

FIGS. 13 and 14 show results of experiments to assess attachment of PEG and α-cyclodextrin to a sensor surface. As illustrated by the differences in impedance shown in FIGS. 13 and 14, PEG and α-cyclodextrin were successfully attached to the sensor surface using the above methodology. FIG. 15 shows results of an EIS serial dilution of resveratrol with a bare electrode surface. FIG. 16 shows results of an EIS serial dilution of resveratrol with a PEG:α-cyclodextrin modified sensor surface. The serial dilutions of FIGS. 15 and 16 were performed in PBS buffer. FIG. 17 shows a comparison of results of EIS serial dilutions of different sensor surfaces. FIG. 18 provides a graph comparing concentration versus Zimag. The results illustrate trends in how the signal changed as concentration of resveratrol increased, indicating a cyclodextrin release from the surface. N=6. FIG. 19A-F provides graphs of results of the serial dilution relating Rct to analyte concentration for each individual electrode indicated in FIG. 18. FIG. 19A-F graphs correspond to points 1-6, respectively, as displayed in FIG. 18. FIG. 20A-C provides graphs of concentration versus relative capacitive change of a single electrode showing a reusability of the sensor towards resveratrol sensing. FIG. 20A shows results from the first use of the sensor, FIG. 20B shows results from the second use of the sensor, and FIG. 20C shows results from the third use of the sensor. FIG. 21A-B shows when the sensor was exposed to cortisol instead of being exposed to resveratrol. Because cortisol does not complex with α-cyclodextrin, no signal is observed in FIG. 21A. FIG. 21B provides a graph of concentration versus relative capacitive change for the sensor in FIG. 21A. FIG. 22A-D provides graphs of concentration versus relative capacitive change for various sensor controls indicating the response of α-cyclodextrin is specific to only molecules complexed with it. FIG. 22A shows that cortisol does not respond. FIG. 22B shows that the bare electrode has minimal response. FIG. 22C shows that with cortisol without cyclodextrin there is no response. FIG. 22D shows that β-cyclodextrin doesn't interact with a PEG surface. FIG. 23 provides a graph showing the reproducibility for the surface after/before each serial dilution demonstrated in FIG. 20A-C. FIG. 24A-B shows traces and a table. FIG. 24A provides traces of an FTIR signal confirming cyclodextrin being removed and added to the surface. FIG. 24B provides data showing the frequency/cm$^{-1}$ for various functional groups and types of vibration. FIG. 25 provides a graph showing XPS signal confirming that cyclodextrin is being removed from the surface and added to the surface.

While the present disclosure provides embodiments of electrochemical sensors and methods of their use, one skilled in the art will appreciate that other types of sensors may be configured to implement the teachings herein. If non-electrochemical sensors are used, non-electrochemical sensing techniques for monitoring release of cyclodextrin from the sensor may be used. Such techniques include, but are not limited to, optical techniques, fluorescent techniques, surface plasmon resonance, and others.

While the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure. The contents of all literature references, patents, and published patent applications cited throughout this application are incorporated herein by reference in their entirety.

What is claimed is:

1. An electrochemical sensor, comprising:
an electrode comprising a surface modified with a covalently attached monolayer configured to non-covalently attach to cyclodextrin and release cyclodextrin based on contact with a binding analyte.

2. The electrochemical sensor of claim 1, wherein the electrode comprises a metal.

3. The electrochemical sensor of claim 1, wherein the electrode comprises at least one of gold, carbon, platinum, silicon, silicon dioxide, and silver.

4. The electrochemical sensor of claim 1, wherein the monolayer comprises adamantane.

5. The electrochemical sensor of claim 4, wherein the adamantane is attached to cyclodextrin.

6. The electrochemical sensor of claim 1, wherein the monolayer comprises a carboxylic acid.

7. The electrochemical sensor of claim 1, wherein the monolayer comprises at least one of polyethylene glycol (PEG), polypropylene glycol (PPG), and polyisobutylene glycol (PBG).

8. The electrochemical sensor of claim 7, wherein a rotaxane is formed by the non-covalent attachment of cyclodextrin to the at least one of PEG, PPG, and PBG.

9. A method for hydrophobic molecular recognition for electrochemical sensing, comprising:
contacting a sample with an electrochemical sensor comprising a surface modified with a covalently attached monolayer configured to non-covalently attach to cyclodextrin and release cyclodextrin based on contact with a binding analyte; and
monitoring release of cyclodextrin from the surface.

10. The method of claim 9, wherein a means of monitoring the release of cyclodextrin comprises at least one of electrochemical impedance spectroscopy, amperometric monitoring, voltametric monitoring, and potentiometric monitoring.

11. The method of claim 9, further comprising reloading the surface with cyclodextrin.

12. The method of claim 11, wherein reloading the surface comprises:
rinsing the surface with an organic solvent, the organic solvent comprising at least one of dimethyl sulfoxide (DMSO), methanol, ethanol, chloroform, dimethylformamide (DMF), and tetrahydrofuran (THF); and
contacting the rinsed surface with a cyclodextrin solution.

13. The method of claim 12, further comprising:
modifying the surface with adamantane using a thiol self-assembled monolayer with a tris(2-carboxyethyl) phosphine (TCEP) reducing agent.

14. The method of claim 13, wherein modifying the surface comprises:
contacting the surface with the adamantane-thiol mixture.

15. The method of claim 14, further comprising:
after contacting the surface with the adamantane-thiol mixture, rinsing the contacted surface with an organic solvent, the organic solvent comprising at least one of DMSO, methanol, ethanol, chloroform, DMF, and THF.

16. The method of claim 15, further comprising:
confirming attachment of adamantane to the rinsed surface by performing at least one of:
quartz crystal microbalance (eQCM); and
electrochemical impedance spectroscopy (EIS).

17. The method of claim 15, further comprising:
contacting the rinsed surface with a cyclodextrin solution to create the electrochemical sensor comprising the surface modified with the covalently attached monolayer configured to non-covalently attach to cyclodextrin and release cyclodextrin based on contact with a binding analyte.

18. The method of claim 9, wherein:
the monolayer comprises at least one of polyethylene glycol (PEG), polypropylene glycol (PPG), and polyisobutylene glycol (PBG); and
a rotaxane is formed by the non-covalent attachment of cyclodextrin to the at least one of PEG, PPG, and PBG.

19. A method of generating an electrochemical sensor capable of performing a cyclodextrin interaction, comprising:
modifying a surface of an electrochemical sensor with covalently attached adamantane configured to non-covalently attach to cyclodextrin and release cyclodextrin based on contact with a binding analyte; and
non-covalently attaching cyclodextrin to the adamantane.

* * * * *